(12) United States Patent
Fidacaro et al.

(10) Patent No.: US 8,737,048 B2
(45) Date of Patent: *May 27, 2014

(54) MODULES FOR MONITORING PATIENTS AND RELATED SYSTEMS AND METHODS

(75) Inventors: James Fidacaro, Mountain Lakes, NJ (US); James Patrick Thrower, Oakland, NJ (US); Geoffrey C. Jawidzik, Mahwah, NJ (US); Nicholas Barker, Laguna Beach, CA (US); Allan Cameron, Natick, MA (US); Jim Wilson, Norwood, MA (US); Hilary Farnsworth, Mamaroneck, NY (US); David Chastain, Boston, MA (US)

(73) Assignee: Mindray DS USA, Inc., Mahwah, NJ (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/597,612

(22) Filed: Aug. 29, 2012

(65) Prior Publication Data

US 2014/0031637 A1 Jan. 30, 2014

Related U.S. Application Data

(63) Continuation of application No. 12/862,489, filed on Aug. 24, 2010, now Pat. No. 8,279,586.

(60) Provisional application No. 61/236,800, filed on Aug. 25, 2009.

(51) Int. Cl.
*G06F 1/16* (2006.01)

(52) U.S. Cl.
USPC .. 361/679.01; 600/300; 345/173; 340/870.01

(58) Field of Classification Search
CPC combination set(s) only.
See application file for complete search history.

(56) References Cited

U.S. PATENT DOCUMENTS

| | | | |
|---|---|---|---|
| 5,375,604 A | 12/1994 | Kelly et al. | |
| 5,640,953 A | 6/1997 | Bishop et al. | |
| 5,936,539 A | 8/1999 | Fuchs | |
| 6,247,674 B1 * | 6/2001 | Jawidzik | 248/213.2 |
| 7,499,272 B2 | 3/2009 | Searby et al. | |
| 8,169,304 B2 | 5/2012 | Schuman, Sr. et al. | |
| 8,233,272 B2 * | 7/2012 | Fidacaro et al. | 361/679.04 |
| 8,279,586 B2 * | 10/2012 | Fidacaro et al. | 361/679.01 |
| 8,334,768 B2 * | 12/2012 | Eaton et al. | 340/539.13 |
| 2002/0188181 A1 | 12/2002 | Boit et al. | |
| 2009/0005651 A1 | 1/2009 | Ward et al. | |
| 2011/0148622 A1 | 6/2011 | Judy et al. | |
| 2011/0148624 A1 | 6/2011 | Eaton et al. | |
| 2011/0152629 A1 | 6/2011 | Eaton et al. | |

OTHER PUBLICATIONS

Notice of Allowance mailed Aug. 17, 2012 as received in U.S. Appl. No. 12/862,489.
Office Action mailed Jun. 26, 2012 as received in U.S. Appl. No. 12/862,489.

* cited by examiner

*Primary Examiner* — Lisa Lea Edmonds
(74) *Attorney, Agent, or Firm* — Kory D. Christensen; Stoel Rives LLP

(57) ABSTRACT

Patient monitoring systems can include a display unit and a patient parameter module. The patient parameter module can be connected to a docking region so as to communicate with the display unit in two or more orientations.

29 Claims, 17 Drawing Sheets

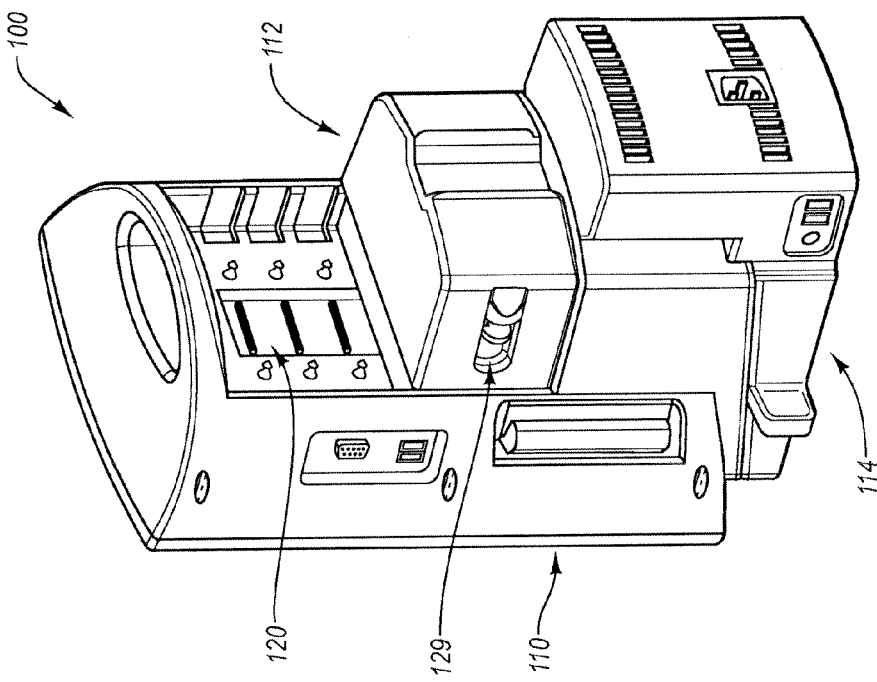
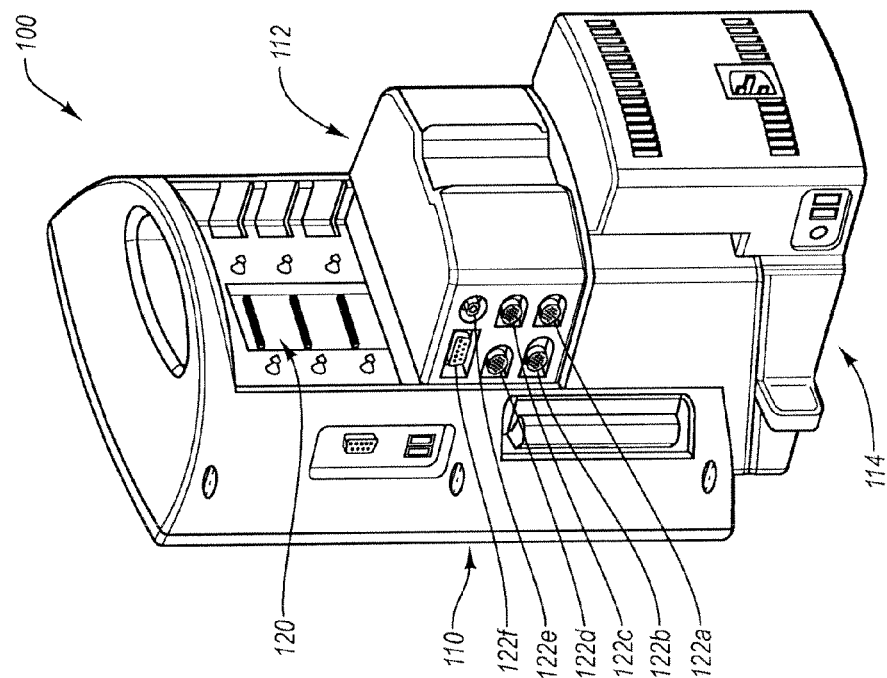

MODULES FOR MONITORING PATIENTS AND RELATED SYSTEMS AND METHODS

CROSS-REFERENCE TO RELATED APPLICATIONS

This application is a continuation of pending U.S. patent application Ser. No. 12/862,489, titled MODULES FOR MONITORING PATIENTS AND RELATED SYSTEMS AND METHODS, filed on Aug. 24, 2010, which claims the benefit under 35 U.S.C. §119(e) of pending U.S. Provisional Patent Application No. 61/236,800, titled MODULES FOR MONITORING PATIENTS AND RELATED SYSTEMS AND METHODS, filed on Aug. 25, 2009. The entire contents of the foregoing are incorporated by reference herein.

TECHNICAL FIELD

The present disclosure relates to patient monitoring.

SUMMARY

Embodiments of modules for use in monitoring patients, as well as related systems and methods, are disclosed.

BRIEF DESCRIPTION OF THE DRAWINGS

FIG. 1A is a rear perspective view of an embodiment of a display system with an embodiment of a patient parameter module coupled with an embodiment of a display unit in a first orientation;

FIG. 1B is a rear perspective view of the display system of FIG. 1A with the patient parameter module coupled with the display unit in a second orientation;

DETAILED DESCRIPTION

Devices for monitoring physiological or other parameters of a patient, such as body temperature, venous oxygen saturation, or blood pressure, are often mounted near the patient. Certain devices can communicate with sensors positioned on or within the patient via one or more wires or cables that extend between the monitoring devices and the patient. The cables are routed to the same portions of the mounted devices independent of the position of the patient relative to the devices. Thus, in many instances, the routing path of the cables or wires can be inconvenient or cumbersome, such as when the patient is at one side of a mounted device and cables are routed to an opposite side of the device.

In certain embodiments disclosed herein, systems for use in monitoring patients are readily reconfigurable to permit wires or cables to be routed to different portions of the devices, as desired. In particular embodiments, the systems can be transitioned among multiple orientations. For example, a module can be configured to be selectively connected with and disconnected from a docking region of a display unit, which may be mounted in a substantially fixed position. The module can be connected with the docking region in either a first orientation, in which one or more communication cables can be routed to one side of the docking region, or a second orientation, in which the communication cables can be routed to a different side of the docking region. In some cases, a module can be selectively coupled with the display unit in any of a variety of configurations, which can improve the routing of cables between the patient and the display unit.

With reference to FIGS. 1A and 1B, in certain embodiments, a patient monitoring system or a display system 100 comprises a display unit 110, a patient parameter module 112, and a base 114. The module 112 can be configured to selectively couple with and decouple from the display unit 110, and the display unit 110 can be configured to selectively couple with and decouple from the base 114. The coupling between the module 112 and the display unit 110, or between the display unit 110 and the base 114, can be mechanical, electrical, optical, and/or of any other suitable variety. For example, the coupling can be for physical union, communication, and/or power transfer.

Figure 2:
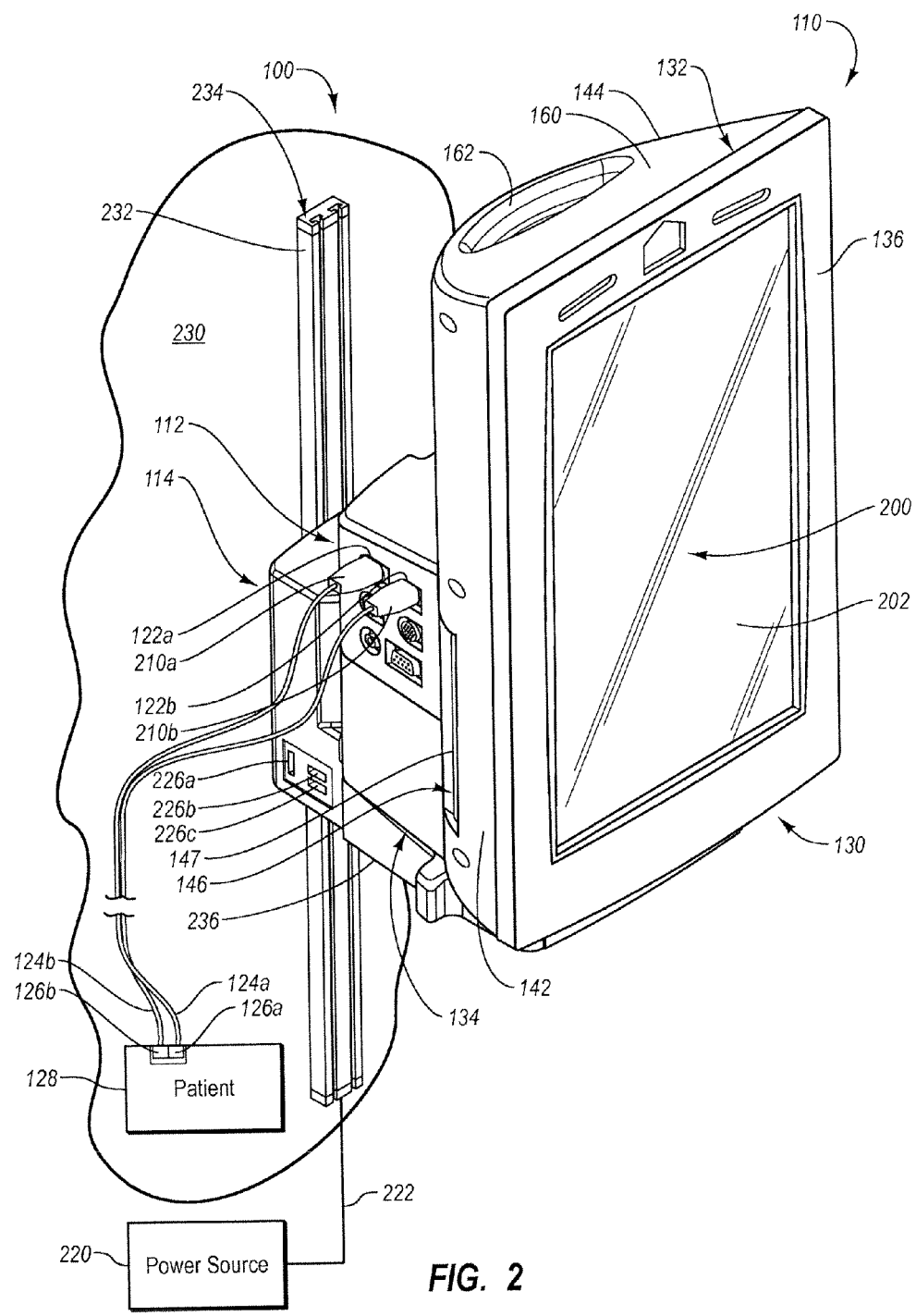
FIG. 2 is a front perspective view of the display system of FIG. 1A in a mounted configuration and coupled with a patient.

FIG. 1A illustrates an embodiment of the display system 100 in a first coupled configuration in which the display unit 110 is connected to the base 114 and in which the module 112 is connected to a docking region 120 of the display unit 110. The module 112 includes a plurality of connectors or ports 122a, 122b, 122c, 122d, 122e, 122f, which can be configured to couple with one or more wires or cables 124a, 124b (FIG. 2). As further discussed below, the cables 124 can extend between the ports 122 and one or more sensors 126a, 126b (FIG. 2), which can be configured to gather data regarding a patient 128 (FIG. 2).

The display system 100 can be configured to be mounted in a substantially fixed position, and the module 112 can be configured to transition from a first orientation relative to the display unit 110 (FIG. 1A) to a second orientation relative to the display unit 110 (FIG. 1B) without moving the display unit 110 or base 114 from the substantially fixed position. As a result, the module 112 can be conveniently manipulated to allow for cables 124 to be run to one side the display unit 110 or another side of the display unit 110 substantially without moving or repositioning the display unit 110 itself. In the illustrated embodiment, when the module 112 is transitioned from the first orientation to the second orientation, the ports 122 are moved from one side of the display unit 110 to an opposite side of the display unit 110. Thus, the ports 122 are not visible in the view depicted in FIG. 1B.

In the illustrated embodiment, the module 112 includes an actuator 129. As further discussed below, actuation of the actuator 129 can allow removal of the module 112 from the display unit 110, and thus can aid in transitioning the module 112 between the first and second orientations.

Figure 3:
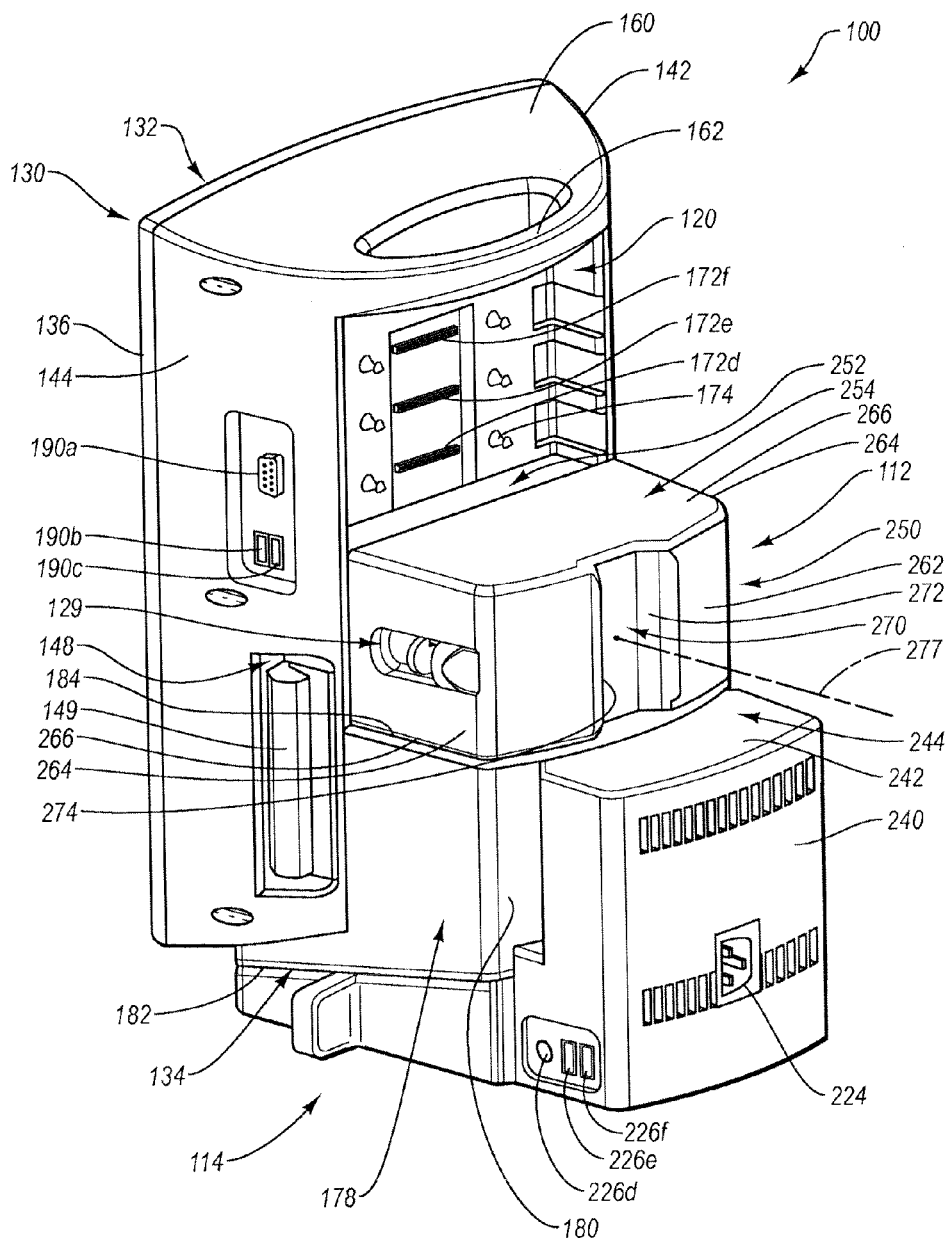
FIG. 3 is a rear perspective view of the display system of FIG. 1A further illustrating an axis of rotation of the patient parameter module.

FIGS. 2 and 3 illustrate front and rear perspective views, respectively, of an embodiment of the system 100 in which the module 112 and the display unit 110 are in a coupled configuration (e.g., the module 112 is in the second orientation of FIG. 1B), and in which the display unit 110 and the base 114 are in a coupled configuration. Portions of the illustrated embodiment that are identifiable in this arrangement will now be described.

The display unit 110, which can also be referred to as a monitor or a display and control unit, comprises a housing 130. The housing 130 defines an upper end 132 and a lower end 134. Extending downwardly from the upper end 132 is a front face 136. The housing 130 can extend rearward from an outer edge of the front face 136. In the illustrated embodiment, a left side face 142 and a right side face 144 each extend rearward from the front face 136. The left and right side faces 142, 144 also extend inwardly towards a central longitudinal plane of the housing 130 so as to be substantially hidden from view from a vantage point directly in front of the front face 136 of the housing 130. Each of the left and right side faces 142, 144 can substantially resemble a portion of a cylinder.

As used herein, terms describing the orientation of an object, such as left, right, upper, lower, front, rear, etc. are recited from a perspective looking toward the front face 136 of the illustrated embodiment of the display unit 110 when the system 100 is in a fully coupled configuration. Such directional terms are used for convenience and should not be construed as limiting.

With continued reference to FIGS. 2 and 3, a left recess 146 extends from the left side face 142 toward an interior of the housing 130, and a right recess 148 extends from the right side face 144 toward the interior of the housing 130. The left and right recesses 146, 148 can include therein a left actuator 147 and a right actuator 149, respectively. The actuators 147, 149 can be used to decouple the display unit 110 from the base 114.

A top face 160 of the housing 130 can extend rearward from the front face 136. In the illustrated embodiment, the housing 130 defines a handle 162 that extends rearward and inwardly from the top face 160 and the left and right side faces 142, 144.

As shown in FIG. 3, a rear portion of the housing 130 can define the docking region 120, which can include one or more communication ports or connectors 172a, 172b, 172c, 172d, 172e, 172f (see also FIG. 5) and one or more mounting pins 174. The docking region 120 is described in greater detail below.

The housing 130 can further define a rearward projection 178. The rearward projection 178 can extend inwardly and rearward from the left and right side faces 142, 144, and can terminate in a rearward end 180 (see also FIG. 5). The rearward projection 178 can include a substantially planar bottom face 182 (see also FIG. 5) and a substantially planar top face 184, and can resemble a trapezoidal prism.

The display unit 110 can include one or more ports 190a, 190b, 190c for receiving or delivering information. The ports 190 can include one or more serial ports, USB ports, Ethernet ports, DVI ports, or any other suitable variety of ports, interfaces, or connectors. In the illustrated embodiments, the ports 190 are recessed relative to the right side face 144.

With reference again to FIG. 2, a front surface of the display unit 110 can include a viewing area 200 that is configured to display information in a visually perceivable format. For example, the viewing area 200 can include a screen 202 of any suitable variety, including those presently known and those yet to be devised. For example, the screen 202 can comprise a liquid crystal display (LCD) panel. In some embodiments, the screen 202 can be configured to receive information or otherwise interact with a medical practitioner. For example, the screen 202 can comprise a touch screen. In some embodiments, information received via one or more of the ports 190 can be displayed on the screen 202.

At least a portion of the information displayed by the display unit 110 can represent information received from the patient 128 or that otherwise relates to the patient 128. For example, in some embodiments, the one or more sensors 126 are connected to the patient 128 to sense one or more parameters, and information obtained via the one or more sensors 126 is delivered to the module 112. In the illustrated embodiment, the sensors 126a, 126b deliver information to the module 112 via the cables 124a, 124b, which are connected to the ports 122a, 122b via connectors 210a, 210b. Although two sets of sensors 126, cables 124, connectors 210, and ports 122 are shown, more or fewer sets are possible.

The ports 122 can comprise any suitable variety of ports, interfaces, or connectors. In some embodiments, one or more of the ports 122 are compatible with one or more specific sensors 126. For example, in some embodiments, the sensors 126 and ports 122 can be configured to deliver information to the module 112 regarding one or more of the electrical activity of the heart, body temperature, blood pressure, venous oxygen concentration, and carbon dioxide concentration of the patient 128. One or more of the ports 122 thus can comprise, for example, an electrocardiogram (ECG) connector, a temperature connector, an invasive and/or noninvasive blood pressure connector, and a mixed venous oxygen concentration ($SVO_2$) connector.

The one or more ports 122 of a module 112 can be described as communication passageways, or paths through which one or more of information, data, impulses, signals, or other communications are communicated to or from the module 112. The connectors 210 may also be described as communication passageways, and may be said to permit wired or tethered communication. Stated otherwise, in some instances, the ports 122 allow the transfer of data along a path that passes through the ports 122.

The module 112 can be configured to process the information it receives from a sensor 126 and to deliver it to the display unit 110, which can display the processed information. In some embodiments, the display unit 110 can further process the information prior to displaying it.

In some embodiments, the system 100 comprises more than one module 112. For example, a single module 112 can be configured to monitor one or more parameters of the patient 128, and one or more additional patient parameter modules 112 each can be configured to monitor one or more additional parameters of the patient 128. In further embodiments, one or more patient parameter modules 112 are only indirectly connected to the patient 128. For example, rather than communicating with the patient via cables 124, the module 112 can instead receive information regarding the patient 128 via a connection with the display unit 110. In some embodiments, the module 112 can comprise a recorder that is configured to store information regarding the patient, which the recorder receives from the display unit 110.

With continued reference to FIGS. 2 and 3, in some embodiments, the display unit 110 can receive power from the base 114, which itself can receive power from a power source 220 via a power line or cord 222. The power source 220 can comprise, for example, the AC wiring of a hospital. As shown in FIG. 3, the base 114 can include a socket 224 for coupling with a power cord 222. In some embodiments, the module 112 can receive power from the display unit 110, as further discussed below.

With continued reference to FIGS. 2 and 3, the base 114 can comprise one or more ports 226a, 226b, 226c, 226d, 226e, 226f for receiving or delivering information. The ports 226 can comprise any suitable variety of ports, interfaces, or connectors. The base 114 and display unit 110 can be coupled so as to communicate with each other such that information received via one or more of the ports 226 can be delivered to the display unit 110. Likewise, the display unit 110 can transmit information via one or more of the ports 226. At least one of the ports 226 can be configured to interface with a hospital network.

With reference to FIG. 2, the base 114 can be mounted in a substantially fixed position. For example, the base 114 can be fixedly mounted to a wall within a hospital room in a single position by one or more plates, brackets, screws, bolts, or other mounting hardware and attachment devices. As another example, the base 114 can be configured to transition among multiple fixed positions. For example, in the illustrated embodiment, the base 114 is coupled to a mounting strip 232, which is in turn mounted to a wall 230 of a hospital room. The base 114 is capable of being adjusted upwardly or downwardly along a path constrained by one or more channels 234 defined by the mounting strip 232 so as to transition among a variety of positions. In each such position, the base 114 can be fixed relative to the mounting strip 232. In some embodiments, the base 114 is coupled with the mounting strip 232 via a mounting plate or a mounting bracket (not shown), the position of which can be adjusted upwardly or downwardly within the channels 234 in any suitable manner.

In other embodiments, the base 114 can be secured to a hospital bed, a mechanical arm, a rolling stand, or any other suitable object (not shown). In some embodiments, a bottom surface 236 of the base 114 is positioned at a height of from about five feet to about six feet above a floor of a hospital room so as to allow the display unit 110 to be viewed easily and/or to avoid interference with other objects in the room.

The base 114 can comprise a component tower 240 that extends upwardly at a rearward end thereof. In the illustrated embodiment, a top surface 242 of the component tower 240 is substantially coplanar with the top face 184 of the rearward projection 178 of the display unit 110 when the base 114 and the display unit 110 are coupled to each other. The component tower 240 can provide a clearing or a space 244 rearward of the module 112 when the module 112 is coupled with the display unit 110. As further discussed below, this arrangement can facilitate the coupling and decoupling of the module 112 to and from the docking region 120 of the display unit 110.

Figure 4A:
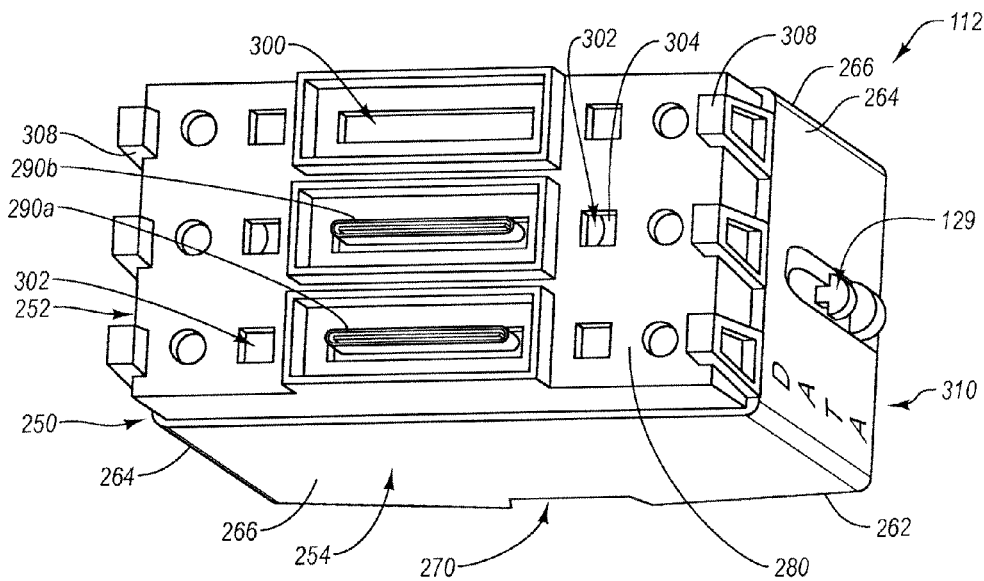
FIG. 4A is a front perspective view of the patient parameter module of FIG. 1A shown disconnected from the display unit.

With reference to FIGS. 3 and 4A, in certain embodiments, the module 112 comprises a housing 250, which can include a front section 252 and a rear section 254. In the illustrated embodiment, substantially all of the front section 252 of the housing 250 is configured to be received within the docking region 120 when the module 112 is connected to the display unit 110. The front and rear sections 252, 254 can cooperate to encase the circuitry and electrical components of the module 112.

The rear section 254 of the housing 250 can define a rearward face 262, two side faces 264, and two transverse faces 266. The rearward face 262 and the side faces 264 can substantially conform to the contour of the rearward projection 178 of the display unit 110 when the module 112 is coupled to the display unit 110. Each of the transverse faces 266 can be substantially planar, and can be configured to rest flatly against the top face 184 of the rearward projection 178 when the module 112 is in one of the first orientation and the second orientation.

In the illustrated embodiment, the rear face 262 defines a channel or recess 270, which can extend in a substantially longitudinal direction between the transverse faces 266. The recess 270 can be at least partially defined by a pair of opposing sidewalls 272, 274. The sidewall 274 closest to the side face 264 that comprises the actuator 129 can aid in single-handed coupling of the module 112 to the display unit 110, which in some cases can advantageously allow for the coupling or decoupling of the module 112 without disturbing any cables that may be connected to the module 112.

For example, in the embodiment illustrated in FIG. 3, a practitioner standing in front of or toward the right side of the system 100 can use his or her right hand to effectuate release of the module 112 from the display unit 110. One or more fingers or fingertips of the right hand can be inserted into the recess 270, and can grip against the left-facing (as illustrated) sidewall 274. The thumb of the right hand can be positioned on the actuator 129, and can move the actuator rearward to permit release of the module 112 from the display unit 110. The module 112 can then be urged rearward and away from the docking region 120. The procedure can be reversed to couple the module 112 with the display unit 110, although in some embodiments, the coupling can take place without actuation of the actuator 129.

The left hand can be used in a similar manner to connect or disconnect the module 112 to or from the display unit 110, such as when the module 112 is moved into or out of the first orientation (shown in FIG. 1A). In further instances, either the right or left hand can be positioned such that one or more fingertips actuate the actuator 129 and the thumb is placed on the sidewall 274.

The space 244 above the component tower 240 can aid in the coupling and decoupling procedures just described. For example, when the base 114 is mounted near a wall 230 (see FIG. 2), the space 244 can permit movement of a hand between the module 112 and the wall 230, as well as movement of the module 112 outward from the docking region 120.

With continued reference to FIG. 3, the module 112 can be transitioned between the first and second orientations by rotation about an axis 277. In the illustrated embodiment, the axis 277 is substantially parallel to the transverse faces 266, and the axis 277 extends between the transverse faces 266 and the side faces 264. The axis 277 can be substantially normal to a front face 280 (see FIG. 4A) of the module 112.

In the illustrated embodiment, the module 112 is rotated through an angle of approximately 180 degrees about the axis 277 when it is transitioned from the first orientation to the second orientation. Stated otherwise, the second orientation is rotated about the axis 277 by approximately 180 degrees relative to the first orientation. As further discussed below, in some embodiments, a variety of other rotation angles are possible for the module 112.

With reference to FIG. 4A, the module 112 can comprise one or more communication ports or connectors 290a, 290b.

The connectors 290 can comprise any suitable variety of port, connector, or interface, and can be complementary to the connectors 172. In certain embodiments, the module 112 comprises an unpopulated connector bay 300, which can serve as a placeholder. The use of an unpopulated bay 300 with the module 112 can result from inclusion of components within the module 112 that consume a relatively large volume, but use relatively few electrical contacts for communication with the display unit 110.

In the illustrated embodiment, the connectors 290a, 290b can be connected with the connectors 172a, 172b of the docking region 120 (see FIG. 5), respectively. This coupling configuration can yield the arrangement depicted in FIG. 3, in which the actuator 129 is at a right side of the system 100. The module 112 can be rotated so as to attach the connectors 290a, 290b to the connectors 172c, 172b (see FIG. 5), respectively. In this orientation, the actuator 129 is at an opposite side of the system 100 and one of the transverse faces 266 is adjacent to the top face 184 of the rearward projection 178 of the display unit 110. Thus, the connectors 290a, 290b can populate different connectors 172 when the module 112 is in the same position relative to the display unit 110, but is rotated about the axis 277 by approximately 180 degrees, due to the absence of a connector from the bay 300. In further arrangements, the connectors 290a, 290b can be coupled, respectively, with the connectors 172b, 172c (actuator 129 faces right); 172d, 172c (actuator 129 faces left); 172c, 172d (actuator 129 faces right); 172e, 172d (actuator 129 faces left); 172d, 172e (actuator 129 faces right); and 172f, 172e (actuator 129 faces left).

The front face 280 of the module 112 can define one or more openings 302 through which the enlarged tip of a mounting pin 174 (FIGS. 3 and 5) can be received. A latch 304 can be positioned behind the front face 280 and can be biased toward the left, in the configuration shown in FIG. 4A, so as to constrict the size of one or more of the openings 302. Accordingly, the tip of one or more mounting pins 174 can be held within the module 112 by the latch 304 to thereby maintain the module 112 connected to the mounting region 120.

Rearward translation of the actuator 129 can cam the latch 304 to move to the right, thereby enlarging the opening 302 to permit passage of the tip of the mounting pin 174 through the opening 302, and thus permit removal of the module 112 from the mounting region 120. The module 112 can include a plurality of protrusions or guides 308 that are configured to aid in coupling the module 112 with the mounting region 120.

In the illustrated embodiment, the module 112 comprises a display region 310 that includes a display that is oriented so as to be read equally well in either the first orientation or the second orientation, or stated otherwise, so as to be substantially without preference for either of the first or second orientations. Matter within the display region 310 can be aligned along a line that is substantially parallel to the axis of rotation 277 (FIG. 3). For example, each letter of the text "DATA" in the illustrated embodiment is rotated by 90 degrees relative to a vertical axis. The display region 310 can include text, symbols, graphics, or other directionally sensitive markings.

Figure 4B:
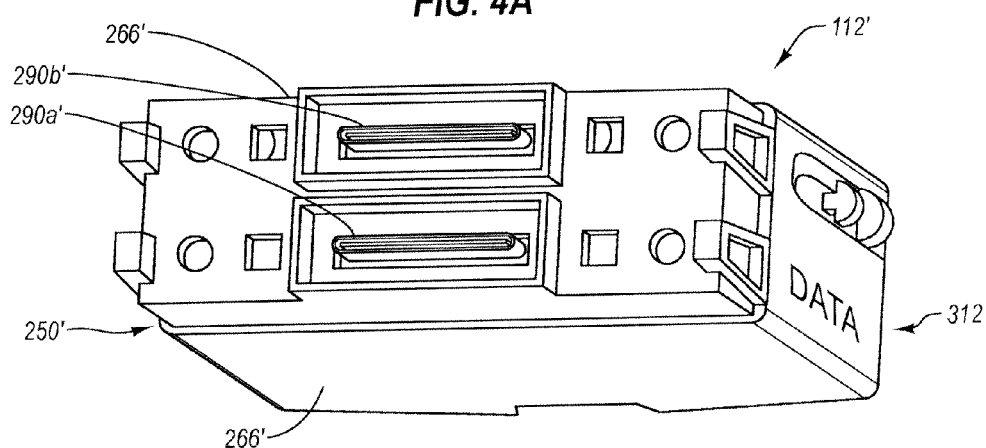
FIG. 4B is a front perspective view of another embodiment of a patient parameter module.

FIG. 4B illustrates an embodiment of a module 112' that resembles the module 112 in many respects. Accordingly, like features are identified with like, yet primed, reference numerals. The module 112' also differs from the module 112 in some respects. For example, the module 112' comprises a housing 250' that is smaller than the housing 250, in that transverse faces 266' of the module 112' are closer to each other than are the transverse faces 266 of the module 112. Likewise, the module 112' does not include a bay 300 that is void of connectors. Rather, the module 112' is sized such that its two connectors 290a', 290b' can be coupled with two connectors 172 of a docking region without the module 112' preventing access to any of the other connectors 172.

Additionally, the module 112' is configured for use in only a single upright orientation. For example, the module 112' can include gravity-sensitive equipment that will not function if the module 112' is rotated upside-down. Accordingly, in some embodiments, the module 112' can comprise a display region 312 that defines an upright orientation that corresponds with the upright orientation of the module 112'. For example, in the illustrated embodiment, the text "DATA" is upright when the connector 290b' is above the connector 290a', but is upside-down when the connector 290a' is above the connector 290b'. The display region 312 thus exhibits a preference for the former orientation. In other embodiments, the module 112' can be configured for use in multiple orientations, and thus may more closely resemble the module 112 (e.g., may include a display region such as the display region 310). In further embodiments, the module 112' can comprise more or fewer connectors 290'.

Figure 4C:
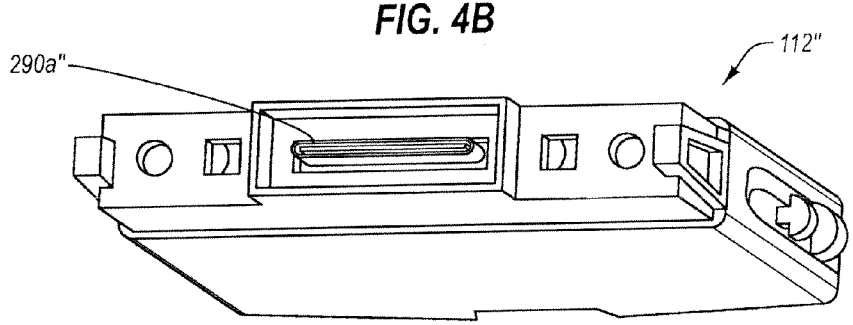
FIG. 4C is a front perspective view of another embodiment of a patient parameter module.

FIG. 4C illustrates an embodiment of a module 112" that resembles the modules 112, 112' in many respects. However, the module 112" comprises only a single connector 290a". Additionally, the module 112" defines a lower profile, without any empty bays 300, and thus will not obstruct any connectors 172 above or below a connector 172 of a docking region 120 to which the connector 290a" may be attached. In some embodiments, the module 112" is configured for use in a single upright orientation, and in others, it may be rotated into one of multiple configurations. In further embodiments, the module 112' can comprise more or fewer connectors 290".

Figure 5:
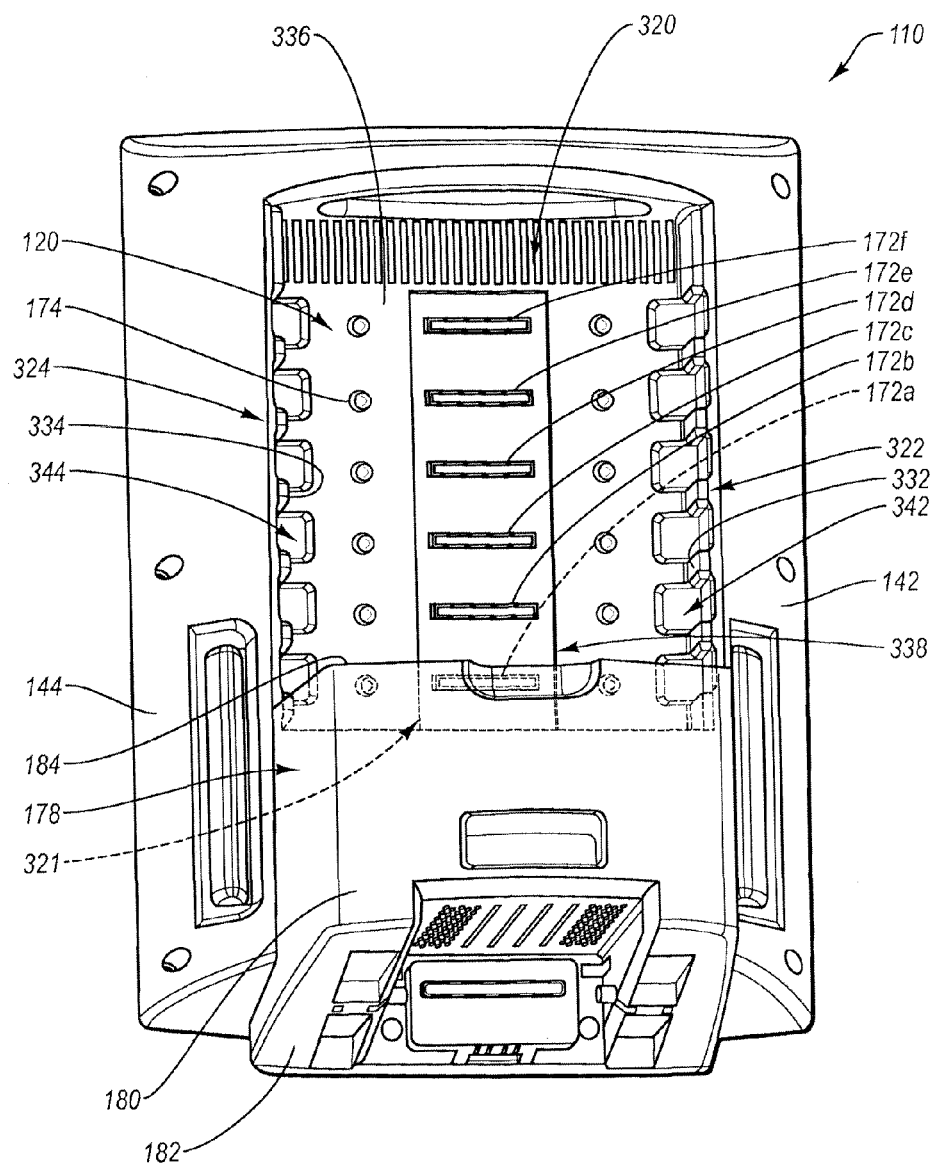
FIG. 5 is a rear perspective view of the display unit of FIG. 1A shown disconnected from the patient parameter module.

FIG. 5 illustrates an embodiment of the docking region 120 of the display unit 110. The docking region 120 can include an upper side 320, a lower side 321, a left side 322, and a right side 324. At the left side 322 of the docking region 120, a left sidewall 332 extends forwardly from a rear edge of the left side face 142 of the display unit 110. Likewise, at the right side 324 of the docking region 120, a right sidewall 334 extends forwardly from a rear edge of the right side face 144 of the display unit 110. Each of the left and right sidewalls 332, 334 extends to a base wall 336. The sidewalls 332, 334, the base wall 336, and the top face 184 of the rearward projection 178 cooperate to form a module receptacle or cavity 338.

The left sidewall 332 and the base wall 336 can define a plurality of left channels 342, and the right sidewall 334 and the base wall 336 can define a plurality of right channels 344. One or more of the left and right channels 342, 344 can be complementary to or otherwise configured to receive and/or retain one or more of the guides 308 of the module 112.

In the illustrated embodiment, the docking region 120 includes six connectors 172. In some embodiments, the connectors 172 are substantially identical to each other, and may be self-symmetrical or rotationally redundant such that a module 112 can be connected with any of the connectors 172, whether in the first orientation or the second orientation. In the illustrated embodiment, each of the modules 112, 112', 112" can be coupled with the docking region 120 simultaneously. The modules 112, 112', 112" can be arranged in any suitable permutation, such as, for example, those shown in TABLE 1.

TABLE 1

| Upper Portion of Docking Region | | Intermediate Portion of Docking Region | | Lower Portion of Docking Region | |
|---|---|---|---|---|---|
| Module | Port Direction | Module | Port Direction | Module | Port Direction |
| 112 | Left | 112' | Left | 112" | Left |
| 112 | Right | 112' | Left | 112" | Right |
| 112 | Right | 112' | Right | 112" | Right |
| 112 | Left | 112" | Left | 112' | Left |
| 112 | Right | 112" | Right | 112' | Left |
| 112 | Right | 112" | Right | 112' | Right |
| 112' | Left | 112 | Left | 112" | Left |
| 112' | Left | 112 | Right | 112" | Right |
| 112' | Right | 112 | Right | 112" | Right |

As noted above, and as shown in illustrative TABLE 1, in some embodiments, it is preferable not to flip, rotate, or reorient the module 112'. In other embodiments, the module 112' can operate in a flipped or rotated orientation.

The docking region 120 can be configured to receive information from one or more modules 112 via the connectors 172, and the information can be used by the display unit 110. For example, coupling one or more connectors 290 of a module 112 with one or more connectors 172 of the docking region 120 can communicatively link the module 112 with the docking region 120. Information can be transferred between the module 112 and the display unit 110, or can be provided from the module 112 to the display unit 110, via the docking region 120 when the connectors 290, 172 are engaged with each other.

The one or more modules 112 can comprise unique identification information, which can be transmitted to the display unit 110 when the modules 112 are coupled to the docking region 120. For example, a module 112 may be configured to communicate its manufacturer, model number, serial number, date of manufacture, previous date of use, monitoring configuration (e.g., identification of the patient parameter it is configured to monitor), or other such information, which may be stored in memory. The display unit 110 may be able to display this information via the screen 202 (FIG. 2).

Moreover, coupling a module 112 with the display unit 110 may prompt the display unit 110 to display other information. For example, if the module 112 is configured to be used in only a single upright orientation, but the module 112 has been connected with the display unit 110 in an upside-down orientation, the module 112 and/or display unit 110 may be able to detect this error and cause a warning to be displayed on the screen 202.

The display unit 110 may also obtain information regarding which connectors 172 are in use or are otherwise obstructed or rendered unavailable. The display unit 110 may further identify which modules 112 are responsible for the usage or obstruction of the connectors 172. Thus, in some embodiments, upon connection of the module 112 illustrated in FIG. 4A with the display unit 110, the display unit 110 may indicate that three of its connectors 172 are rendered unavailable by the module 112.

As previously discussed, information regarding the one or more parameters of the patient 128 that are being monitored by the modules 112 can be delivered to the display unit 110 via the docking region 120. The display unit 110 can display this information via the screen 202.

Figure 6A:
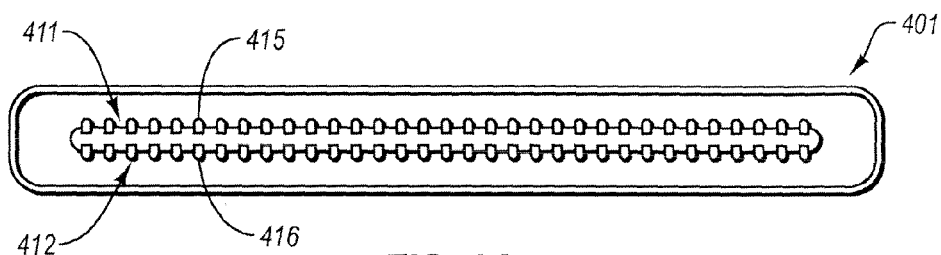
FIG. 6A is an end-on plan view of an embodiment of a connector compatible with embodiments of the system of FIG. 1A.
Figure 6B:
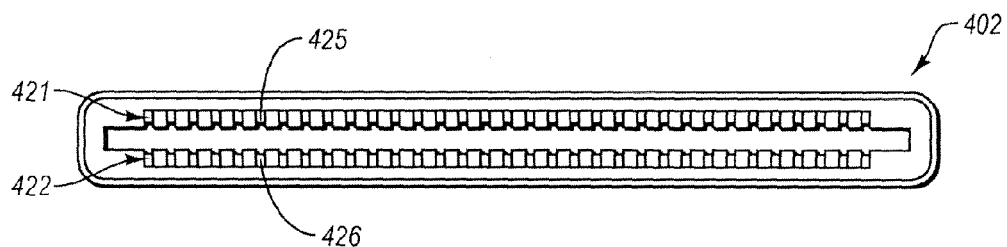
FIG. 6B is an end-on plan view of an embodiment of a connector configured to couple with the connector of FIG. 6A.

FIGS. 6A and 6B illustrate an embodiment of a pair of complementary connectors 401, 402 suitable for use with certain embodiments of the system 100. Either connector 401, 402 can be used as one or more of the connectors 172 (FIG. 5) and/or as one or more of the connectors 290, 290', 290" (FIGS. 4A-4C). In the illustrated arrangement, each connector 401, 402 is substantially self-symmetrical such that a top half and a bottom half thereof are substantially identical to each other.

With reference to FIG. 6A, the connector 401 comprises a first electrical interface 411 and a second electrical interface 412. The first electrical interface 411 comprises a top row of electrical contacts 415, and the second electrical interface 412 comprises a bottom row of electrical contacts 416. The electrical contacts 415, 416 can comprise any suitable structure for electrical communication, such as metallic pins, leads, slots, plugs, or sockets. Moreover, any suitable number or arrangement of the electrical contacts 415, 416 is possible. With reference to FIG. 6B, the connector 402 comprises a first electrical interface 421 that includes a top row of electrical contacts 425, and comprises a second electrical interface 422 that includes a bottom row of electrical contacts 426.

For the sake of convenience, the following discussion focuses on embodiments of a system 100 in which the connector 290a" of the module 112" (FIG. 4C) comprises the connector 401, and in which the connector 172a of the docking region 120 (FIG. 5) comprises the connector 402. Similar embodiments are discussed with respect to the connectors illustrated in FIGS. 6A, 6B, 7A, 7B, 8A, 8B, 8C, 9A, 9B, 9C, 10A, 10B, 11A, 11B, 12A, and 12B. Although the module 112" and the docking region 120 are not shown in these figures (except that a portion of the docking region 120 is shown in FIG. 11B), the discussion relating to these figures nevertheless references the module 112" and the docking region 120. For all embodiments, appropriate reversals of the connectors associated with the connector 290a" and of the connectors associated with the connector 172a are possible. Likewise, the connectors can be used with embodiments of the modules 112 and 112' (FIGS. 4A and 4B).

With continued reference to FIGS. 6A and 6B, in some embodiments, the electrical interface 411 of the connector 401 is not used. For example, the electrical contacts 415 may not be connected to any circuitry within the module 112". When the module 112" is connected to the docking region 120 in a first orientation, the interface 412 and the interface 422 couple with each other. In particular, the electrical contacts 416 of the interface 412 contact the electrical contacts 426 of the interface 422. When the module 112" is transitioned to a second orientation, the interface 412 and the interface 421 couple with each other. In particular, the electrical contacts 416 of the interface 412 contact the electrical contacts 425 of the interface 421.

In other embodiments, one of the interfaces 421, 422 of the connector 402 may not be used, and both of the interfaces 411, 412 of the connector 401 may be used. Thus, for example, in a first coupling orientation of the module 112", the interface 411 and the interface 421 may be coupled with each other, and in a second coupling orientation of the module 112", the interface 412 and the interface 421 may be coupled with each other.

Figure 7A:
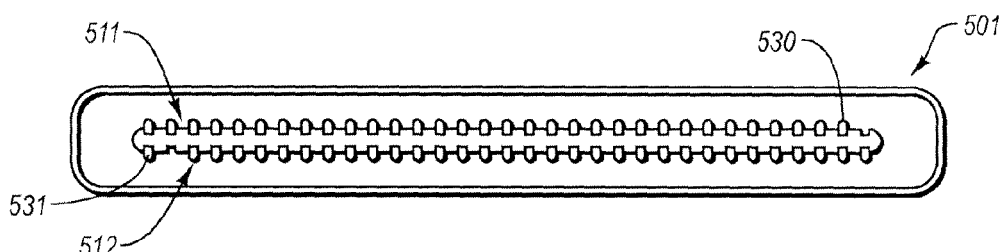
FIG. 7A is an end-on plan view of another embodiment of a connector compatible with embodiments of the system of FIG. 1A.
Figure 7B:
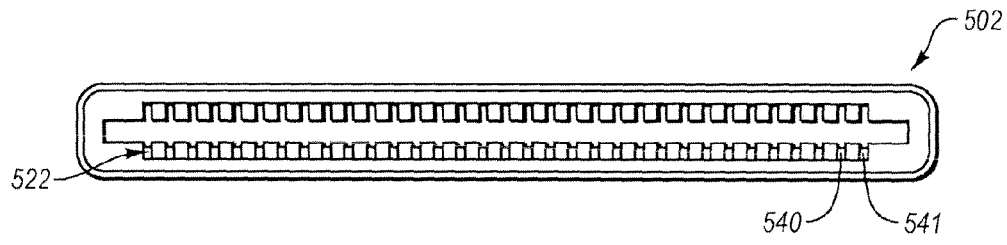
FIG. 7B is an end-on plan view of an embodiment of a connector configured to couple with the connector of FIG. 7A.

FIGS. 7A and 7B illustrate an embodiment of complementary connectors 501, 502, which can resemble the connectors 401, 402. Accordingly, similar features are identified with like references numerals having an incremented leading digit. In the illustrated embodiment, electrical contacts that are not utilized are not shown. In some embodiments, these omitted contacts are not physically present, while in other embodiments, these omitted contacts may in fact be physically present, but merely left unwired or disconnected. The preceding discussion regarding numbering conventions and depiction of electrical contacts applies equally to FIGS. 8A, 8B, 8C, 9A, 9B, 9C, 10A, 10B, 11A, 11B, 12A, and 12B.

A first connection interface 511 of the connector 501 can include an electrical contact 530 at an end thereof. A second connection interface 512 can include an electrical contact 531 at an end thereof. When the connectors 501, 502 are coupled in a first orientation, the contact 531 can communicate with an electrical contact 541 of an interface 522 of the second connector 502. However, no communication between the connectors 501, 502 is made via an electrical contact 540 of the connector 502 in this operational configuration. Similarly, when the connectors 501, 502 are coupled in a second orientation, the contact 530 can communicate with the contact 540, but no communication is made via the contact 541. The physical absence of an electrical contact in each of the interfaces 511, 512 or, in other embodiments, the different wiring of the interfaces 511, 512, are examples of asymmetries that can indicate whether the module 112" is in a first orientation or a second orientation.

Figure 8A:
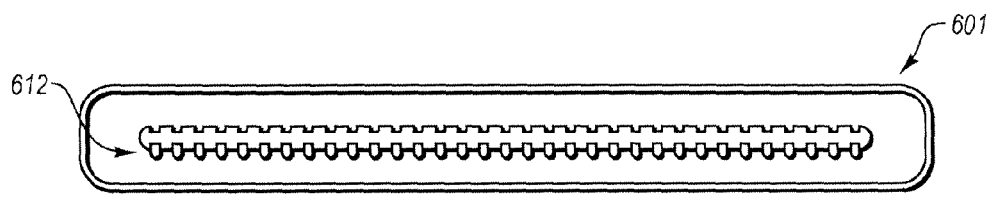
FIG. 8A is an end-on plan view of another embodiment of a connector compatible with embodiments of the system of FIG. 1A.
Figure 8B:
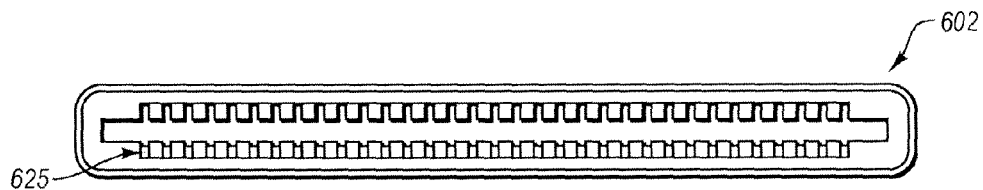
FIG. 8B is an end-on plan view of an embodiment of a connector configured to couple with the connector of FIG. 8A.
Figure 8C:
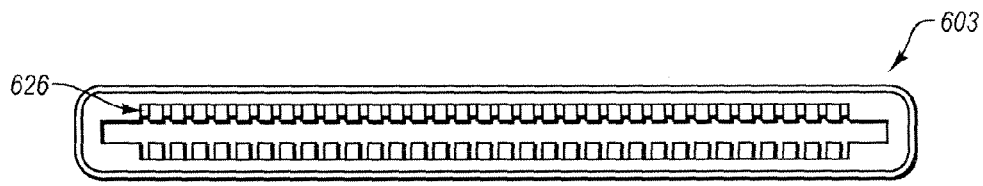
FIG. 8C is an end-on plan view of another embodiment of a connector configured to couple with the connector of FIG. 8A.

FIGS. 8A, 8B, and 8C illustrate an embodiment of a connector 601 and embodiments of two discrete connectors 602, 603 with which the connector 601 can be coupled. The connector 602 includes a lower electrical interface 625 and the connector 603 includes an upper electrical interface 626. Each of the connectors 602, 603 can be separately mounted to the docking region 120. Any relative angle of rotation between the mounted connectors 602, 603, and hence the interfaces 625, 626, is possible. For example, in the illustrated embodiments, the rotational angle between the two orientations of the interfaces 625, 626 is 180 degrees, In various embodiments, the rotation angle can be between about 45 degrees and about 315 degrees, between about 60 degrees and about 300 degrees, between about 90 degrees and about 270 degrees, between about 135 degrees and about 225 degrees, no less than about 30 degrees, no less than about 45 degrees, no less than about 90 degrees, no less than about 135 degrees, or no less than about 180 degrees. The connector 601 comprises an electrical interface 612 that is configured to couple with each of the interfaces 625, 626, the module 112", and thus the connector 601 likewise can be rotated through the angles just described between coupling states.

Figure 9A:
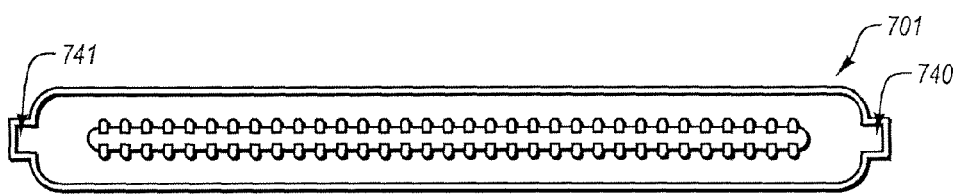
FIG. 9A is an end-on plan view of another embodiment of a connector compatible with embodiments of the system of FIG. 1A.
Figure 9B:
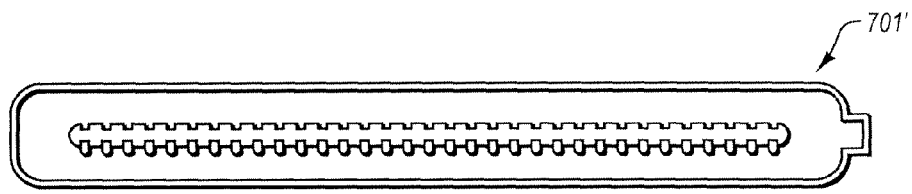
FIG. 9B is an end-on plan view of another embodiment of a connector compatible with embodiments of the system of FIG. 1A.
Figure 9C:
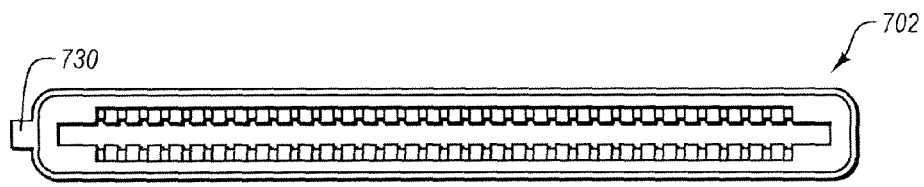
FIG. 9C is an end-on plan view of an embodiment of a connector configured to couple with the connector of FIG. 9A in two separate relative orientations and configured to couple with the connector of FIG. 9B in a single relative orientation.

FIGS. 9A, 9B, and 9C illustrate embodiments of separate connectors 701, 701' that are configured to couple with a connector 702. The connector 702 can be keyed in any suitable manner. In the illustrated embodiment, a protrusion 730 extends from one end of the connector 602.

The connector 701 is configured to couple with the connector 702 in two different orientations. In each orientation, one of a channel 740 and a channel 741 defined by the connector 702 receives the protrusion 730 of the connector 702. The connector 701' comprises a single channel 742 for receiving the protrusion 730 such that the connector 701' can only couple with the connector 702 in a single relative orientation.

In some embodiments, each of the connectors 172 of the docking region 120 comprises a connector such as the connector 702. Some modules 112 that are configured to function well in any orientation may comprise connectors such as the connector 701, whereas other modules that are designed to operate in a preferred orientation (e.g., the module 112') may comprise connectors such as the connector 701'.

Figure 10A:
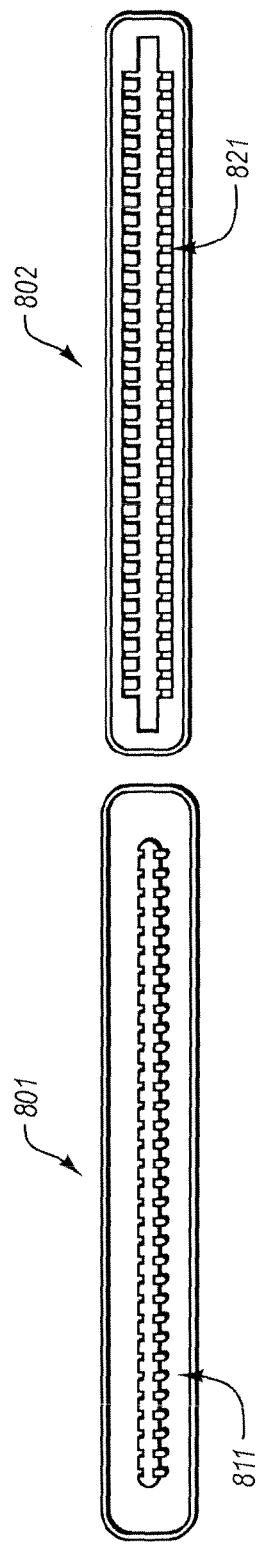
FIG. 10A is an end-on plan view of an embodiment of a pair of connectors that are configured to be coupled with each other and that are compatible with embodiments of the system of FIG. 1A.
Figure 10B:
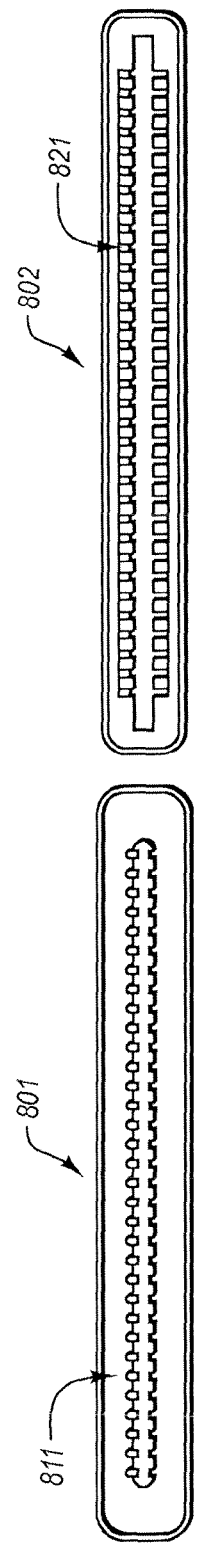
FIG. 10B is an end-on plan view of the pair of connectors of FIG. 10A shown in a rotated state.

FIGS. 10A and 10B depict an embodiment of a pair of connectors 801, 802 that are configured to maintain a relative orientation to one another when the module 112" is rotated between a first and a second orientation. The connector 801 is fixedly attached to the module 112" such that rotation of the module 112" effects rotation of an electrical interface 811 of the connector 801. The connector 802, and an electrical interface 821 thereof, is rotatable relative to the docking region 120.

With reference to FIG. 10A, the connectors 801, 802 are shown in a first coupling orientation. With reference to FIG. 10B, the connectors 801, 802 are shown as having been rotated to a second orientation. In particular, the connectors 801, 802 have both been rotated by the same amount.

In some embodiments, the connector 802 can be rotated through a range of orientations, and can remain substantially fixed in any position to which it has been rotated. For example, the connector 802 can be mounted to the docking region 120 via a self-tensioning axle. In various embodiments, the connector 802 can be configured to rotate through a range of angles of from 0 degrees to no more than about 360 degrees, no more than about 270 degrees, no more than about 180 degrees, no more than about 90 degrees, or no more than about 45 degrees. In other embodiments, the connector 802 can be rotated to any of a variety of discreet orientations within the foregoing ranges, such as via one or more detents. In still other embodiments, the connector 802 is fixedly mounted in the docking region 120 and the connector 801 is configured to rotate relative to the module 112", such as via any of the manners just described.

Figure 11A:
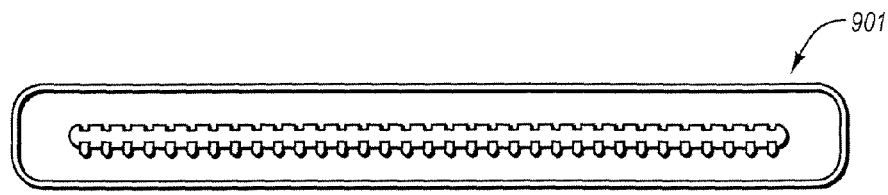
FIG. 11A is an end-on plan view of another embodiment of a connector compatible with embodiments of the system of FIG. 1A.
Figure 11B:
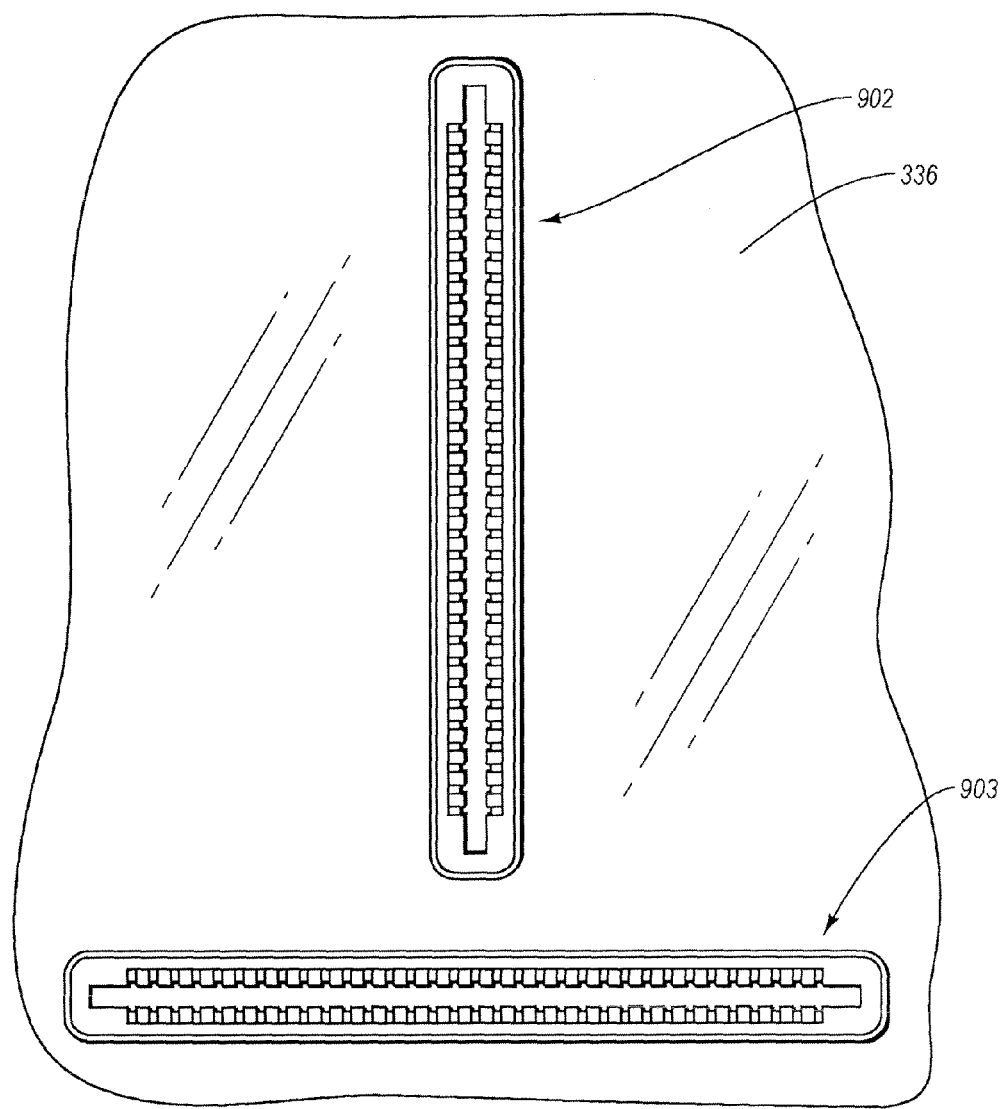
FIG. 11B is an end-on plan view of an embodiment of a pair of connectors configured to separately couple with the connector of FIG. 11A.

FIGS. 11A and 11B depict an embodiment of a connector 901 and two discrete connectors 902, 903 with which the connector 901 can be coupled. The connectors 902, 903 are fixedly mounted to the base wall 336 of the docking region 120, and are elongated in directions that are substantially orthogonal to each other. Other relative angles between the connectors 902, 903, such as any of the angle ranges described above, are also possible. Each connector 902, 903 includes two electrical interfaces, such that the connector 901 can be attached to the docking region 120 in four different orientations. Stated otherwise, the module 112", which may include ports 122 (FIG. 1A) for receiving information from a patient, can be oriented such that the ports 122 are substantially directed toward one of the upper side 320, lower side 321, left side 322, and right side 324 of the docking region 120 (FIG. 5) in separate coupling arrangements.

Figure 12A:
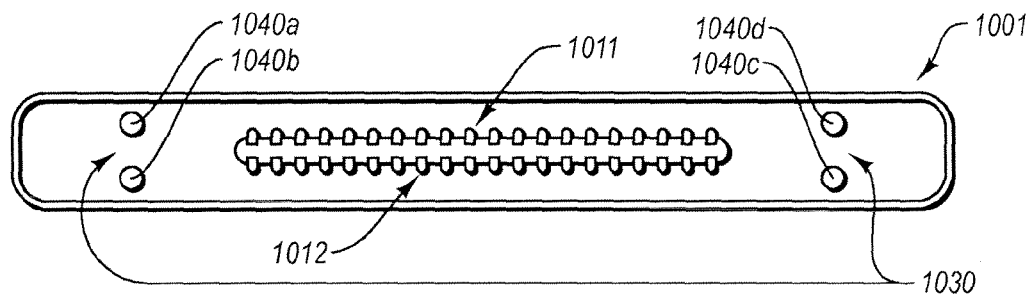
FIG. 12A is an end-on plan view of another embodiment of a connector compatible with embodiments of the system of FIG. 1A.
Figure 12B:
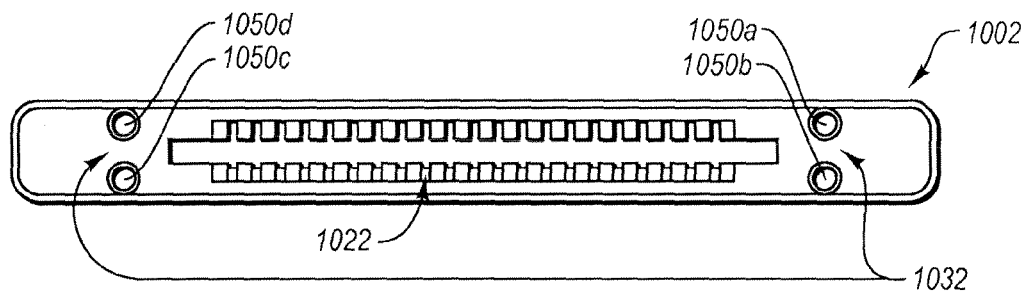
FIG. 12B is an end-on plan view of an embodiment of a pair of connectors configured to separately couple with the connector of FIG. 12A.

FIGS. 12A and 12B depict an embodiment of connectors 1001, 1002 that are configured to couple with each other in two different orientations. The connector 1001 includes first and second electrical communication interfaces 1011, 1012, as well as a third electrical power interface 1030. The connector 1002 includes a communication interface 1022 and a power interface 1032. The power interfaces 1030, 1032 are configured to couple with each other when the connectors 1001, 1002 are coupled in either of the first or second orientations, whereas only one of the communication interfaces 1011, 1012 couples with the communication interface 1022, depending on the coupling state of the connectors 1001, 1002.

In some embodiments, the communication interfaces 1011, 1012, 1022 are used for purposes of communicating information when the connectors 1001, 1002 are attached to each other, and the interfaces 1030, 1032 are used for power transfer. The power interface 1030 can include electrical contacts 1040a, 1040b, 1040c, 1040d and the power interface 1032 can include electrical contacts 1050a, 1050b, 1050c, 1050d. When connected, the contacts 1040a, 1040c, 1050a, 1050c can be at ground, and the contacts 1040b, 1040d, 1050b, 1050d can be at a voltage relative to ground. With respect to power transfer, the connectors 1001, 1002 operate identically in either coupling arrangement (e.g., regardless of whether the contacts 1040a, 1050a or the contacts 1040a, 1050c are coupled).

Figure 13:
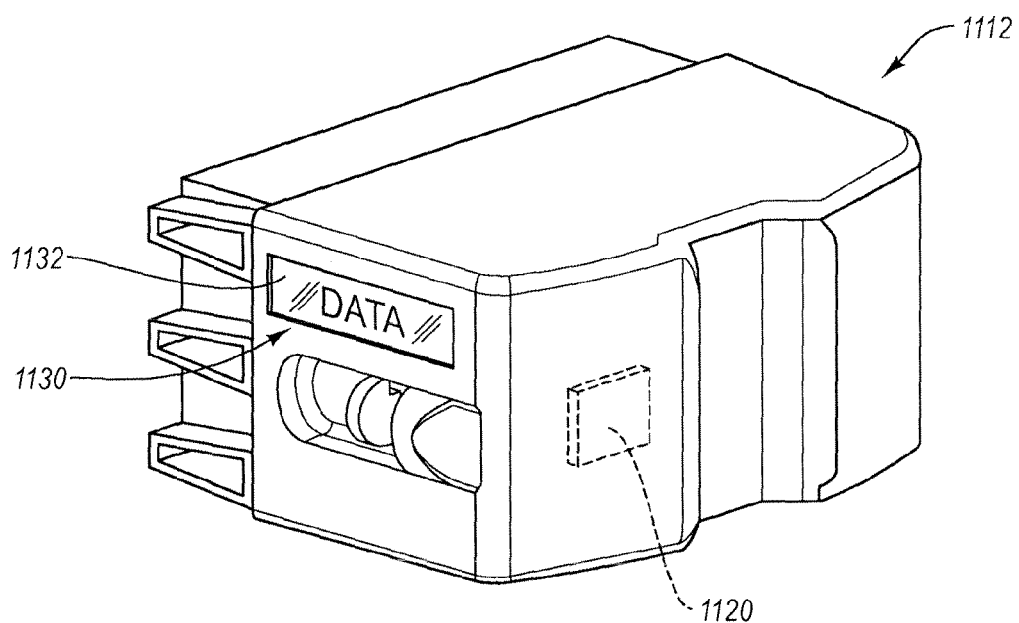
FIG. 13 is a rear perspective view of another embodiment of a patient parameter module.

FIG. 13 depicts an embodiment of a module 1112, such as the modules 112, 112', 112". The foregoing discussion regarding the modules 112, 112', and 112" thus applies to the module 1112, where appropriate. The module 1112 can include a sensor 1120 that is configured to detect one or both of an orientation of the module 1112 and a change in the orientation of the module 1112. For example, the sensor 1120 can comprise any suitable accelerometer.

The module 1112 can include a display region 1130 configured to change based on an orientation of the module 1112. In the illustrated embodiment, the display region 1130 includes a screen 1132. Images can be displayed on the screen 1132 in an upright orientation when the module 1112 is in one orientation, and can also be displayed in an upright orientation when the module 1112 is in a rotated, flipped, opposing, or upside-down orientation. Thus, in the illustrated embodiment, the text "DATA" is shown in an upright orientation, and if the module 1112 were flipped over, the display would be reconfigured such that the text "DATA" would again be upright. Information regarding an orientation of the module 1112 obtained from the sensor 1120 can be used by the module 1112 to change the orientation of the display region 1130. In some embodiments, information regarding an orientation of the module 1112 can be used to alter an electrical interface of the module 1112, as further described below.

Figure 14A:
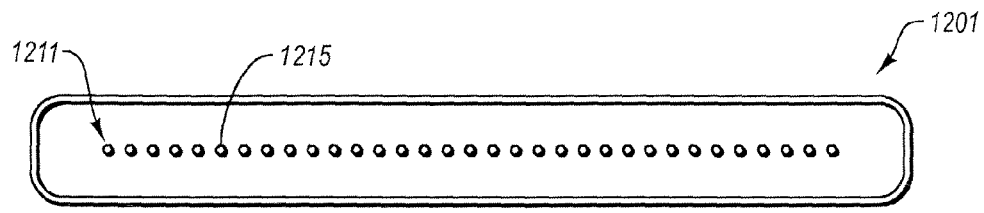
FIG. 14A is an end-on plan view of another embodiment of a connector compatible with embodiments of the system of FIG. 1A.
Figure 14B:
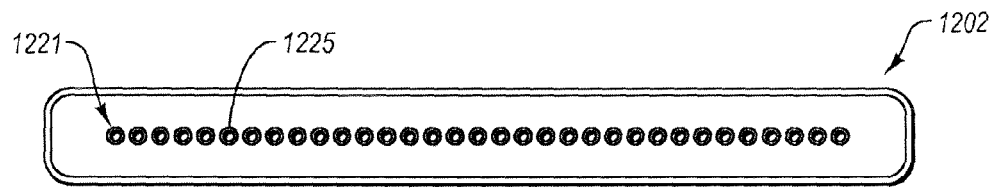
FIG. 14B is an end-on plan view of an embodiment of a connector configured to couple with the connector of FIG. 14A.

FIGS. 14A and 14B illustrate an embodiment of a connector pair 1201, 1202 configured for use with embodiments of the module 1112. With reference to FIG. 14A, the connector 1201 includes an electrical interface 1211 that includes a plurality of electrical contacts 1215. The connector 1201 can be configured to couple with the connector 1202, in two separate orientations. As shown in FIG. 14B, the connector 1202 includes an electrical interface 1221 that includes a plurality of electrical contacts 1225. The electrical interfaces 1211 and 1221 are configured to couple with each other in each of the first and second orientations. However, the second orientation is reversed relative to the first orientation such that different electrical contacts 1215, 1225 are in contact with each other in the second orientation.

The connector 1202 can be fixedly coupled with the docking region 120 (FIG. 5) such that the module 1112 is rotated to transition between the coupling orientations. When the module 1112 is rotated from one coupling orientation to another, information obtained from the sensor 1120 (FIG. 13) indicating that the rotation has occurred can be used by the module 1112 to change an electrical configuration of the electrical interface 1211. In particular, an assignment (e.g., pin assignment) of the electrical contacts 1215 can be reversed so as to maintain agreement between the electrical interfaces 1211, 1221. In other embodiments, information regarding an orientation of the module 1112 can instead reverse an electrical configuration of the interface 1121 of the connector 1102. One or more sets of the electrical contacts 1215, 1225 can be used for power transfer, while one or more of the remaining electrical contacts 1215, 1225 can be used for communication.

Figure 15A:
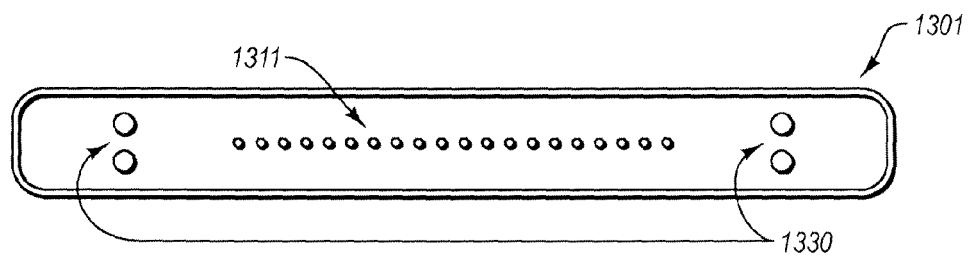
FIG. 15A is an end-on plan view of another embodiment of a connector compatible with embodiments of the system of FIG. 1A.
Figure 15B:
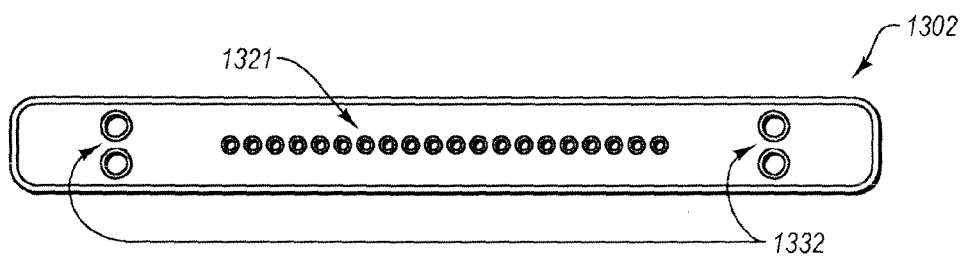
FIG. 15B is an end-on plan view of an embodiment of a connector configured to couple with the connector of FIG. 15A.

FIGS. 15A and 15B illustrate another embodiment of connectors 1301, 1302 that are configured for use with the module 1112. The connectors 1301, 1302 can include electrical interfaces 1311, 1321, respectively, which can operate identically to the electrical interfaces 1211, 1221 just described, although in some embodiments, the electrical interfaces 1311, 1321 are not specifically used for power transfer. The connectors 1301, 1302 can include additional electrical interfaces 1330, 1332, respectively, which can function identically to the power interfaces 1030, 1032 described above with respect to FIGS. 12A and 12B. Accordingly, in some embodiments, each of the electrical interfaces 1311, 1330 is configured to couple with each of the electrical interfaces 1321, 1332, respectively, in each of the first and second coupling orientations. However, unlike an electrical configuration of either the electrical interface 1311 or the electrical interface 1321, an electrical configuration of each of the electrical interfaces 1330, 1332 remains unchanged upon transition of the connectors 1301, 1302 between the two coupling configurations.

Figure 16:
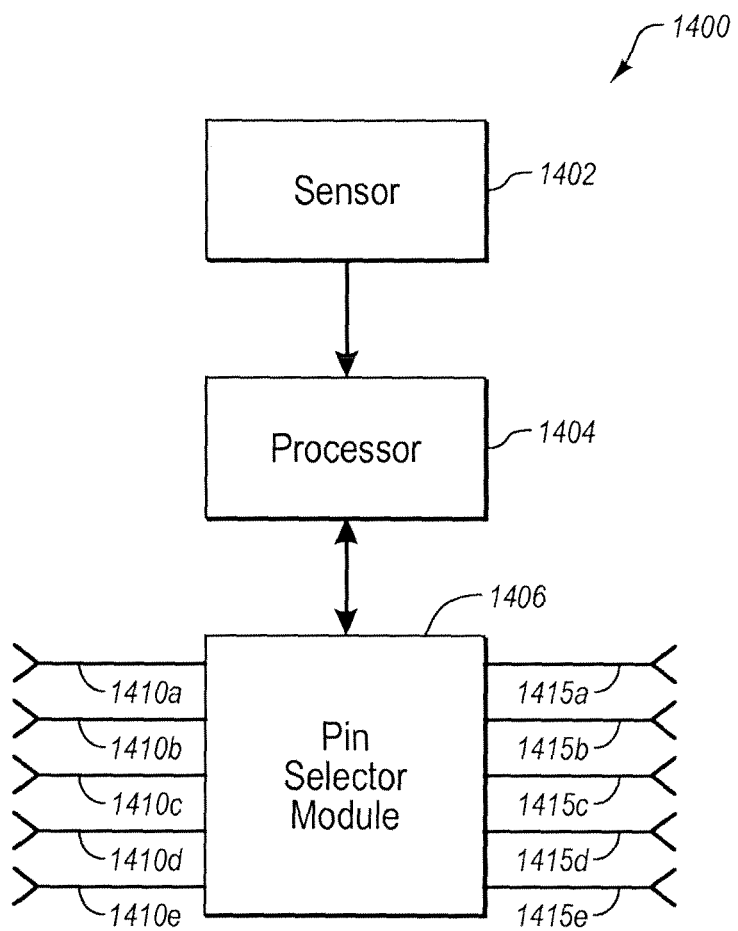
FIG. 16 is a schematic diagram of an embodiment of a system for changing an electrical configuration of an electrical interface.

FIG. 16 is a schematic illustration of an embodiment of a system 1400 for changing an electrical configuration of an electrical interface, such as any of the electrical interfaces 1211, 1221, 1311, 1321 described above. The system 1400 can include a sensor 1402, a processor 1404, and a pin selector module 1406. The processor 1404 can be configured to receive information from the sensor 1402, and can be configured to communicate with the pin selector module 1406. The pin selector module 1406 can receive a plurality of leads 1410, and can be configured to route the leads 1410 to a plurality of electrical contacts 1415 (e.g., the electrical contacts 1215 in FIG. 14A).

The sensor 1402 can comprise any suitable sensor, such as the sensor 1120 described above. Additionally, the sensor can comprise any suitable mechanical device, such as, for example, a physical switch that is activated or moved to a first position when a module is coupled with a docking region in a first orientation and/or deactivated or moved to a second position when the module is coupled with the docking region in a second orientation. Other illustrative examples of sensors are discussed further below.

The processor 1404 can be configured to receive information from the sensor 1120 and to control operation of the pin selector module based on the information. Thus, for example, the processor may instruct the pin selector module to reconfigure a pin assignment of a connector upon receiving information from the sensor 1120 that an orientation of a module has changed. In other embodiments, the system 1400 does not include the processor 1404 and the sensor 1402 provides signals directly to the pin selector module 1406. The pin selector module 1406 thus can be configured to respond directly to signals received from the sensor 1402.

The pin selector module 1406 can comprise any suitable circuitry and/or devices for rerouting electrical paths. For example, in some embodiments, the pin selector module 1406 comprises a multiplexer (line selector) or one or more electrical switches.

Any suitable reassignment of the leads 1410 and the electrical contacts 1415 is possible. For example, in the illustrated embodiment, the electrical contacts 1415 can correspond with the electrical contacts of a connector (such as the connector 1201 of FIG. 14A) that is fixedly secured to a patient parameter module and has only five electrical contacts. When the connector is in a first orientation, the leads 1410a, 1410b, 1410c, 1410d, 1410e can be assigned to the electrical contacts 1415a, 1415b, 1415c, 1415d, 1415e, respectively. However, when the connector is transitioned to a second orientation (such as when the patient parameter module is flipped over), the leads 1410a, 1410b, 1410c, 1410d, 1410e can be reassigned to the electrical contacts, 1415e, 1415d, 1415c, 1415b, 1415a, respectively.

Figure 17A:
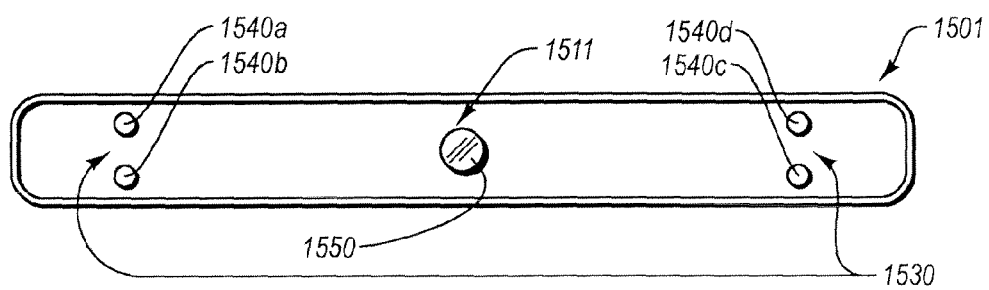
FIG. 17A is an end-on plan view of another embodiment of a connector compatible with embodiments of the system of FIG. 1A.
Figure 17B:
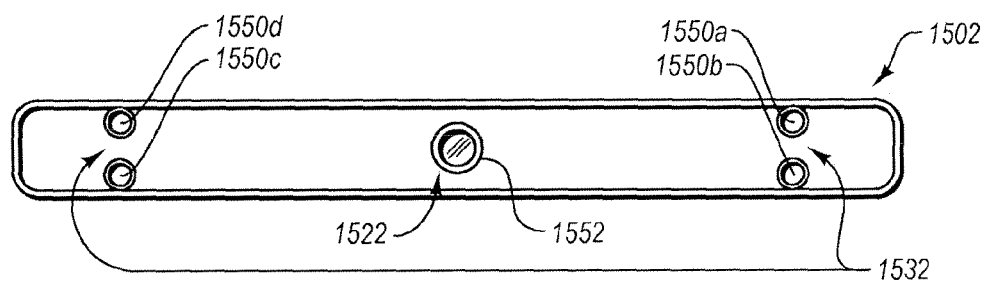
FIG. 17B is an end-on plan view of an embodiment of a connector configured to couple with the connector of FIG. 17A.

FIGS. 17A and 17B illustrate another embodiment of complementary connectors 1501, 1502 that can resemble connectors described above in many respects. For example, the connector 1501 can include an electrical power interface 1530 that includes electrical contacts 1540a, 1540b, 1540c, 1540d, and the connector 1502 can include an electrical power interface 1532 that includes electrical contacts 1550a, 1550b, 1550c, 1550d, in a manner similar to the connectors 1001, 1002 and 1301, 1302. The electrical interfaces 1530, 1532 can be used for transferring power from a display unit to a patient parameter module in manners such as described above.

Rather than having additional electrical interfaces for communicating information, however, the connectors 1501, 1502 instead include complementary non-electrical communication interfaces 1511, 1522, respectively. The communication interfaces 1511, 1522 can be configured to couple with each other so as to communicate signals (e.g., information-carrying signals) in any suitable non-electrical manner. For example, in the illustrated embodiment, the non-electrical interfaces 1511, 1522 comprise optical connectors 1550, 1552 that are configured to couple with each other so as to transmit optical signals. Other information transmission systems are also possible, such as, for example, infrared.

The communication interfaces 1511, 1522 can be configured to couple with each other when the connectors 1501, 1502 are attached to each other in the orientations shown in FIGS. 17A and 17B, as well as when either of the connectors 1501, 1502, is rotated 180 degrees relative to its illustrated orientation. Stated otherwise, the interfaces 1511, 1522 may be configured to couple with each other, and function properly, independent of whether the connectors 1501, 1502 are attached to each other in a first relative orientation or a second relative orientation that is rotationally offset relative to the first relative orientation. The electrical power interfaces 1530, 1532 can operate in a manner such as described with respect to the interfaces 1030, 1032. Accordingly, the connectors 1501, 1502 can readily function when connected to each other in either of two relative orientations.

In view of the foregoing, many connector systems are available to allow wired or tethered communication of information between a patient parameter module and a display unit (or from one such device to the other). For example, the connectors 1501, 1502, which include non-electrical communication interfaces 1511, 1522, can permit such wired or tethered communication. Additionally, certain electrical connectors described above, which instead include electrical interfaces for transmitting data, can allow such wired or tethered communication of information. Stated otherwise, the non-electrical communication interfaces (1511,1522) and the electrical communication interfaces (e.g., the interfaces 1211, 1221 and 1311, 1321) allow information to be delivered from one device to another only when the communication interfaces are coupled with each other. Stated in yet another manner, in certain instances, the communication interfaces allow the transfer of data along a path that passes exclusively through a set of attached connectors.

Figure 18A:
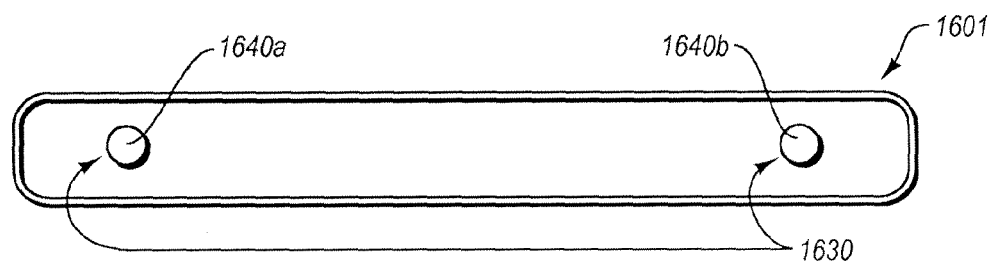
FIG. 18A is an end-on plan view of another embodiment of a connector compatible with embodiments of the system of FIG. 1A.
Figure 18B:
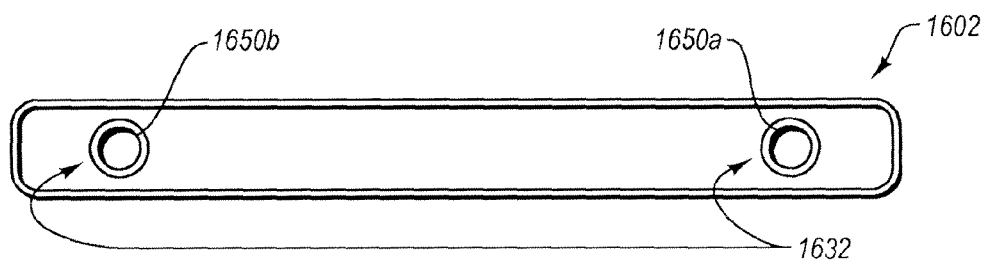
FIG. 18B is an end-on plan view of an embodiment of a connector configured to couple with the connector of FIG. 18A.

FIGS. 18A and 18B illustrate another embodiment of complementary connectors 1601, 1602 that can be used to permit a patient parameter module 112 to be coupled with a display unit 110 in either of a first and a second rotational orientation. The connectors 1601, 1602 comprise complementary power interfaces 1630, 1632. The interfaces 1630, 1632 can be configured to permit a patient parameter module to draw power from a display unit when the module is in either a first or second rotational orientation. In the illustrated embodiment, the power interfaces 1630, 1632 comprise electrical leads 1640a, 1640b, 1650a, 1650b. Other suitable arrangements for the power interfaces 1630, 1632 (as well as other power interfaces disclosed herein) are also possible. For example, in some embodiments, the power interfaces 1630, 1632 comprise magnetic inductance interfaces.

In certain embodiments, such as some embodiments that employ the connectors 1601, 1602, a patient parameter module 112 is configured to communicate wirelessly with a display unit. Any suitable wireless system or protocol may be used, such as, for example, radio frequency (e.g., Bluetooth™, ZigBee, RFID), infrared, magnetic inductance, etc. Stated otherwise, the module 112 may be communicatively linked with the display unit in a wireless or un-tethered manner.

Figure 19A:
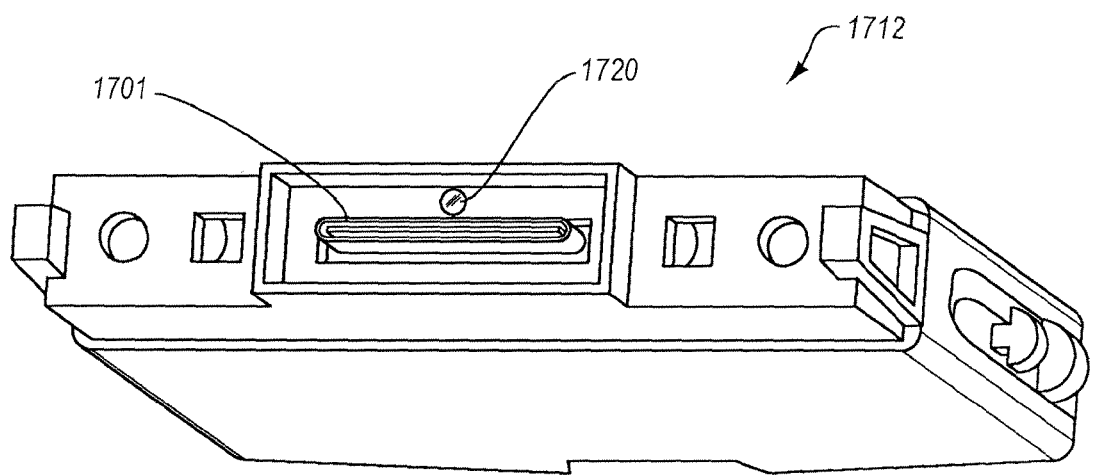
FIG. 19A is a front perspective view of another embodiment of a patient parameter module that includes an optical sensor.
Figure 19B:
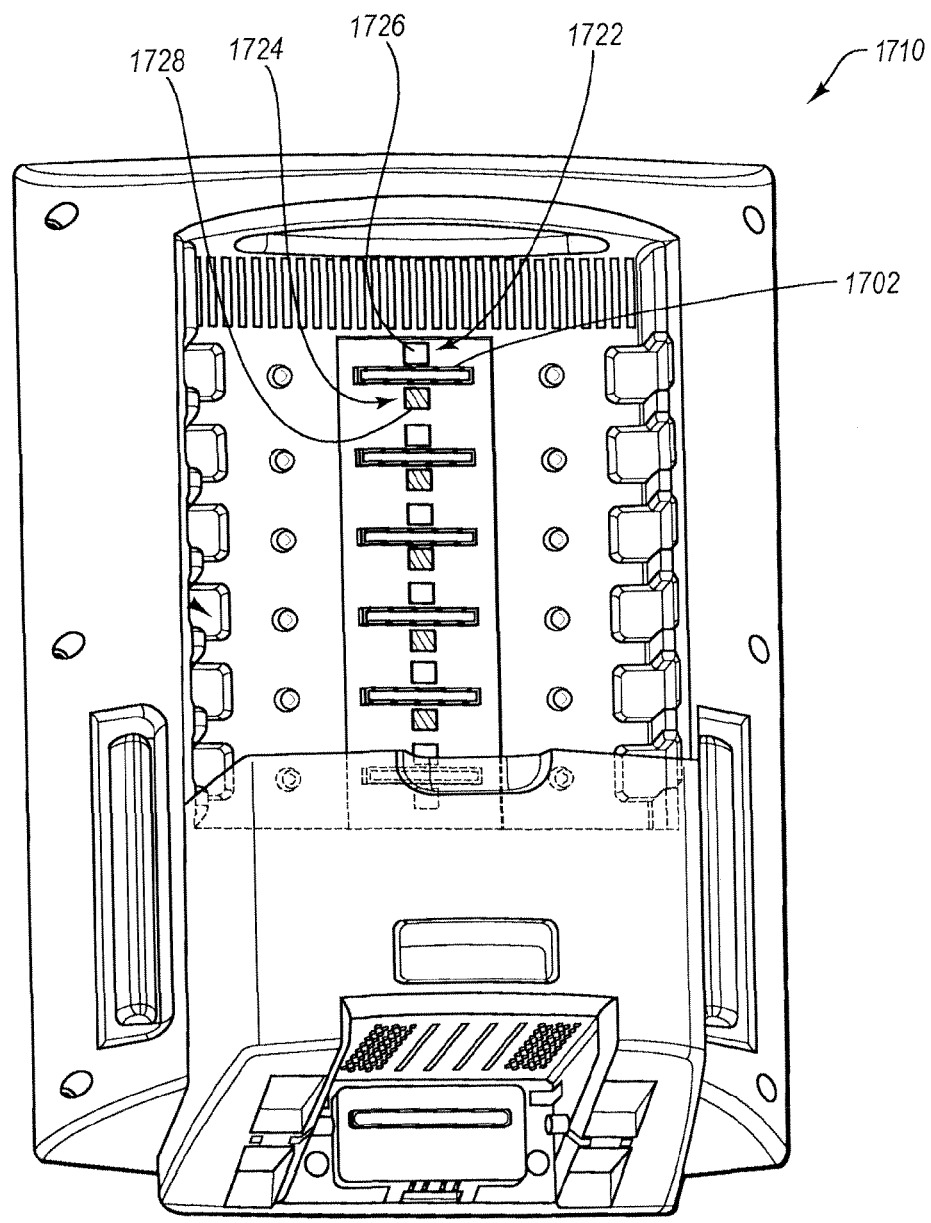
FIG. 19B is a rear perspective view of an embodiment of a display unit that includes optical targets on either side of connectors.

FIG. 19A illustrates an embodiment of a patient parameter module 1712, such as the patient parameter modules 112 discussed above, that is configured to be selectively connected to the display unit 1710 illustrated in FIG. 19B. The module 112 includes a connector 1701 that can resemble any of the connectors described herein. The module further includes an optical sensor 1720. The display unit 1710 includes a plurality of connectors 1702 that are complementary to the connector 1701. In addition, the display unit 1710 includes separate optical targets 1722, 1724 on either side of each connector 1702.

An upper optical target 1722 can vary from a lower optical target 1724 so as to allow the optical sensor 1720 to detect an orientation of the patient parameter module 1712 when the module 1712 is coupled to the display unit 1710. For example, in some embodiments, the upper optical target 1722 comprises a reflector 1726, whereas the lower optical target 1724 comprises a darkened cavity 1728 that reflects much less light than the reflector 1726. A difference in the amount of light reflected by whichever optical target 1722, 1724 is within the view of the optical sensor 1720 can provide a standard for determining the orientation of the module 1712.

Any other suitable system or method may be used to determine an orientation of the module 1712. For example, as previously discussed, in some embodiments, one or more accelerometers may be used. In some embodiments, the display unit 1710 and the module 1712 may each have one or more accelerometers, from which the orientations of the display unit 1710 and the module 1712 relative to each other may be determined. In other embodiments, only the module 1712 may include one or more accelerometers, such that merely its gravity-based orientation may be determined. As previously discussed, orientation information obtained via sensors may be used, for example, in the assignment of electrical contacts (e.g., making pin assignments), in determining the availability of the connectors of a display unit 1710, in determining whether a module 1712 is undesirably upside-down, and/or in providing a representation of the orientation of a module on a display screen 202 (FIG. 2).

Figure 20:
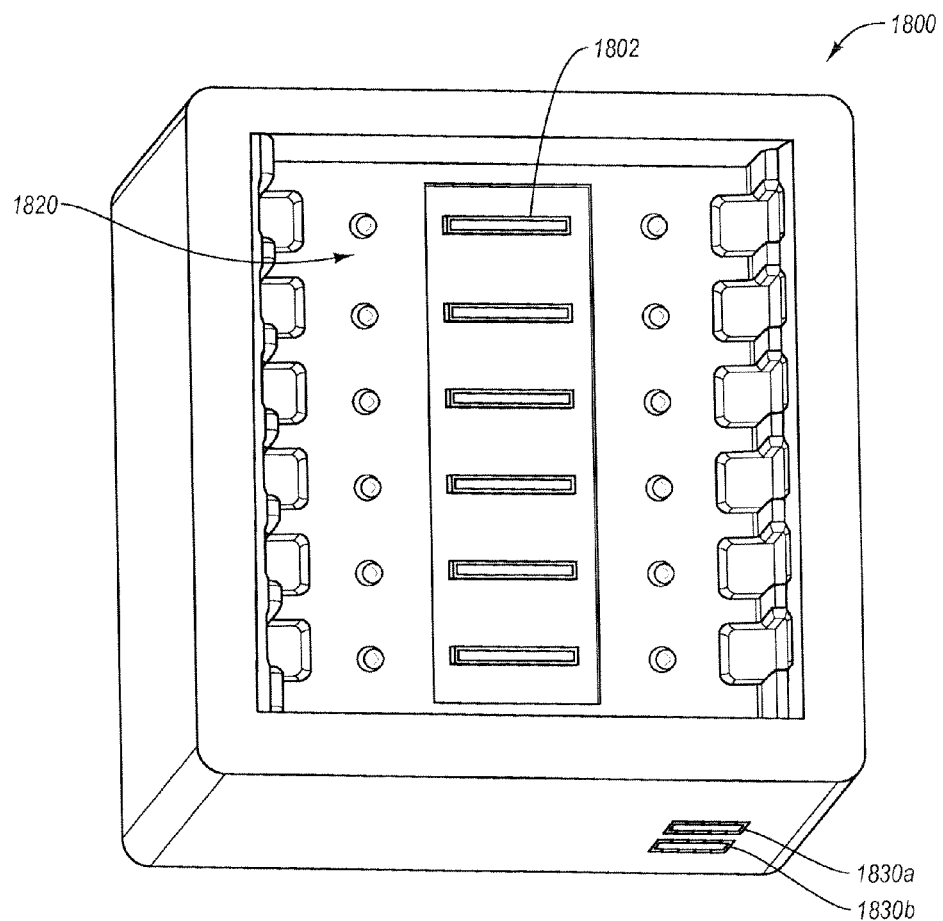
FIG. 20 is a front perspective view of an embodiment of a module rack.

FIG. 20 illustrates an embodiment of a module rack 1800 that is compatible with certain embodiments of the system 100. The rack 1800 can define a docking region 1820 that includes one or more connectors 1802. In the illustrated embodiment, the docking region 1820 is substantially identical to a portion of the embodiment of the docking region 120 illustrated in FIG. 5. Accordingly, relevant portions of the disclosure directed to the docking region 120 are equally applicable to the docking region 1820. For example, the docking region 1820 can be configured to couple with any of the modules 112, 112', 112", 1112, 1712 described herein.

The rack 1800 can be physically separate from the display unit 110 (FIG. 2). In some embodiments, the rack 1800 can be mounted in the vicinity of a patient and/or in the vicinity of a display unit 110 when the display unit 110 is coupled with a mounted base 114 (FIG. 2). For example, the rack 1800 can be mounted to a wall, a hospital bed, a mechanical arm, a rolling stand, or any other suitable object.

The rack 1800 can be configured to electrically communicate with the display unit 110, such as via one or more wires or cables (not shown). For example, in some embodiments, the rack 1800 can include one or more connectors 1830a, 1830b that can be coupled with one or more of the connectors 190 of the display unit 110 (FIG. 3) and/or one or more of the connectors 226 of the base 114 (FIGS. 2 and 3) via cables. In certain of such embodiments, the rack 1800 may be situated a great distance from a display unit 110 with which it is in electrical communication. For example, the rack 1800 may be within a separate room or a separate building from the display unit 110 with which it is coupled.

In some embodiments, the rack 1800 is configured to receive patient parameter modules in addition to those that may be coupled with the docking region 120 of a display unit 110. For example, the rack 1800 can serve as a supplemental receptacle for patient parameter modules. Thus, each of the rack 1800 and the display unit 110 can comprise its own docking region 1820, 120, respectively. In other embodiments, the display unit 110 does not include a docking region 120, and thus information from patient parameter modules is first routed through the rack 1800. In further embodiments, the rack 1800 can be integrated with the base 114.

Further embodiments of the systems and devices disclosed herein are also possible. For example, some embodiments permit a module (e.g., any of the modules 112, 112', 112", 1112) and a docking region (e.g., either of the docking regions 120, 1820) to be coupled with each other in two or more discreet coupling states, three or more discreet coupling states, or four or more discreet coupling states. Further embodiments provide for a continuous range of coupling states. Additionally, as previously discussed, one or more of a module and a docking region can comprise a rotatable connector, in some embodiments. In further embodiments, the module can be separated from the docking region, the connector can be rotated to a new position, and then the module can be reattached to the docking region. In other embodiments, the module and the docking region can remain coupled with each other as the module and the connector are rotated between coupling states. Moreover, in some embodiments rotation of the module between coupling configurations is not constrained about a single axis (e.g., the axis 277 in FIG. 3), but can also rotate about one or more axes that are orthogonal to that axis (e.g., orthogonal to the axis 277).

The foregoing disclosure recites various embodiments that include modules for monitoring patient parameters, docking devices, and coupling devices. Examples of means for monitoring a parameter of a patient include the modules 112, 112', 112", 1112, and 1712. Examples of means for communicating information from a patient to monitoring means include the cables 124, the connectors 210, and/or the ports 122. Examples of means for docking a monitoring means include the docking regions 120, 1820. Examples of means for linking the monitoring means and the docking means include the connectors 172, 290, 290', 290", 401, 402, 501, 502, 601, 602, 603, 701, 701', 702, 801, 802, 901, 902, 903, 1001, 1002, 1201, 1202, 1301, 1302, 1501, 1502, 1601, 1602, 1701, 1702, and 1802.

Methods related to the disclosed patient monitoring systems, such as the system 100, their respective components and features, and their use are supported by this disclosure and will be evident to the skilled practitioner. For example, actions described in this disclosure can form the basis of method steps. Moreover, any suitable combination of actions disclosed with respect to the patient monitoring systems, and their respective components and features, is contemplated by this disclosure.

As used herein, the term "either" does not necessarily refer to two exclusive options, and may include within its scope more options than those explicitly listed. Thus, although a module may be connected with a docking region in either a first orientation or a second orientation, it is also possible that the module may be connected with the docking region in additional orientations.

Additionally, although the foregoing disclosure uses the terms "first" and "second" in describing certain of the illustrated embodiments, these terms are merely used for convenience in describing the illustrated embodiments, and are in no way intended to read limitations into any recitation of the broad terms "first" and "second" in the claims. Likewise, although an orientation may be identified as a "first" orientation in this disclosure, and another orientation may be identified as a "second" orientation, the terms "first" and "second" could be reversed with respect to these orientations.

It will be understood by those having skill in the art that many changes may be made to the details of the above-described embodiments without departing from the underlying principles of the present invention. The scope of the present invention should, therefore, be determined only by the following claims. Elements recited in means-plus-function format are intended to be construed in accordance with 35 U.S.C. §112 ¶ 6.

What is claimed is:

1. A display system comprising:
    a display unit;
    a docking region configured to receive information used by the display unit, the docking region having a first side and a second side; and
    a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations.

2. The display system of claim 1, wherein the display unit comprises the docking region.

3. The display system of claim 1, wherein the docking region comprises a first connector and the module comprises a second connector, and wherein the first and second connectors are configured to couple with each other when the module is in each of the first and second orientations.

4. The display system of claim 3, wherein the module is configured to provide information to the display unit via the first and second connectors when the module is in each of the first and second orientations.

5. The display system of claim 3, wherein the first connector is configured to rotate relative to the docking region or the second connector is configured to rotate relative to the module such that the relative orientation of the first and second connectors is substantially the same for each of the first and second orientations of the module.

6. The display system of claim 3, wherein the first and second connectors are keyed so as to be able to couple with each other in only a single relative orientation.

7. The display system of claim 3, wherein the first connector comprises a first non-electrical interface and the second connector comprises a second non-electrical interface, and wherein the first and second non-electrical interfaces are configured to couple with each other when the module is in each of the first and second orientations.

8. The display system of claim 7, wherein the module is configured to provide information to the display unit via the first and second non-electrical interfaces when the module is in each of the first and second orientations.

9. The display system of claim 1, wherein one of the docking region and the module comprises both a first and a second electrical interface and the other of the docking region and the module comprises a third electrical interface, wherein the first and third electrical interfaces are configured to be coupled with each other when the module is in the first orientation and the second and third electrical interfaces are configured to be coupled with each other when the module is in the second orientation.

10. The display system of claim 9, wherein the first and second electrical interfaces are asymmetrical so as to indicate whether the module is in the first orientation or the second orientation.

11. The display system of claim 9, wherein the docking region comprises a fourth interface and the module comprises a fifth interface, and wherein the fourth and fifth interfaces are configured to couple with each other when the module is in each of the first and second orientations.

12. The display system of claim 1, wherein the docking region comprises an electrical interface, and wherein the module comprises an electrical interface that is configured to couple with the electrical interface of the docking region when the module is in each of the first and second orientations.

13. The display system of claim 12, wherein the module comprises a sensor configured to detect one or both of an orientation of the module and a change in the orientation of the module, and wherein an electrical configuration of the electrical interface of the module is configured to be altered based on a change in the orientation of the module.

14. The display system of claim 13, wherein the electrical interface of the module comprises a plurality of electrical contacts, and wherein movement of the module from the first orientation to the second orientation causes a reassignment of the electrical contacts.

15. The display system of claim 13, wherein the docking region comprises an additional electrical interface, and wherein the module comprises an additional electrical interface that is configured to couple with the additional electrical interface of the docking region when the module is in each of the first and second orientations, and wherein an electrical configuration of the additional electrical interface of the module is configured to remain unchanged upon transition of the module between the first and second orientations.

16. The display system of claim 1, wherein the module comprises an actuator, and wherein actuation of the actuator permits disconnection of the module from the docking region.

17. The display system of claim 16, wherein the actuator and the communication passageway are at opposite sides of the module.

18. The display system of claim 1, wherein the module is configured to be selectively connected with the docking region in one or more additional orientations in which the module is configured to provide information to the display unit via a linkage with the docking region.

19. The display system of claim 1, wherein the module is configured to be rotated by 180 degrees to transition from the first orientation to the second orientation.

20. The display system of claim 1, wherein a rack comprises the docking region, and wherein the rack is configured to electrically communicate with the display unit.

21. The display system of claim 1, wherein the module further comprises a display region configured to display information in each the first and second orientations without a preference for either orientation.

22. The display system of claim 1, wherein the module is configured to be wirelessly communicatively linked with the docking region in each of the first and second orientations.

23. The display system of claim 1, wherein the module comprises a sensor configured to detect one or both of an orientation of the module and a change in the orientation of the module.

24. A system configured to communicate information regarding a patient, the system comprising:
- a docking region; and
- a module configured receive information via at least one communication passageway, the module configured to be selectively mechanically coupled with the docking region and to be selectively decoupled from the docking region, wherein the module is configured to be coupled with the docking region in either a first orientation or a second orientation,
- wherein the docking region comprises a first connector and the module comprises a second connector, and wherein the first and second connectors are configured to couple with each other when the module is in each of the first and second orientations.

25. The display system of claim 24, wherein the module is configured to communicate information to a display unit via the first and second connectors when the module is in each of the first and second orientations.

26. The display system of claim 24, wherein the first connector is configured to rotate relative to the docking region or the second connector is configured to rotate relative to the module such that the relative orientation of the first and second connectors is substantially the same for each of the first and second orientations of the module.

27. A patient parameter module configured to be selectively connected with a docking region in either a first orientation or a second orientation, wherein the docking region comprises a first side and a second side, the patient parameter module comprising:
- a communication passageway configured to receive information regarding a patient from one or more sensors; and
- a connector configured to electrically couple the module with the docking region when the module is in at least one of the first and second orientations,
- wherein when the module is connected to the docking region in the first orientation, the communication passageway is closer to the first side of the docking region than it is to the second side of the docking region, and wherein when the module is connected to the docking region in the second orientation, the communication passageway is closer to the second side of the docking region than it is to the first side of the docking region.

28. The patient parameter module of claim 27, further comprising an actuator configured to permit release of the module from the docking region when actuated.

29. A display system comprising:
- means for monitoring a parameter of a patient, the monitoring means comprising means for communicating information from the patient to the monitoring means;
- means for docking the monitoring means, wherein the docking means defines a first side and a second side; and
- means for linking the monitoring means and the docking means in either a first orientation or a second orientation, wherein the communicating means is closer to the first side of the docking means than it is to the second side of the docking means in the first orientation and the communicating means is closer to the second side of the docking means than it is to the first side of the docking means in the second orientation.

* * * * *

(12) EX PARTE REEXAMINATION CERTIFICATE (11665th)
United States Patent
Fidacaro et al.

(10) Number: US 8,737,048 C1
(45) Certificate Issued: Apr. 3, 2020

(54) MODULES FOR MONITORING PATIENTS AND RELATED SYSTEMS AND METHODS

(75) Inventors: James Fidacaro, Mountain Lakes, NJ (US); James Patrick Thrower, Oakland, NJ (US); Geoffrey C. Jawidzik, Mahwah, NJ (US); Nicholas Barker, Laguna Beach, CA (US); Allan Cameron, Natick, MA (US); Jim Wilson, Norwood, MA (US); Hilary Farnsworth, Mamaroneck, NY (US); David Chastain, Boston, MA (US)

(73) Assignee: SHENZHEN MINDRAY BIO-MEDICAL ELECTRONICS CO. LTD., Nanshan, Shenzhen (CN)

Reexamination Request:
No. 90/014,194, Aug. 29, 2018

Reexamination Certificate for:
Patent No.: 8,737,048
Issued: May 27, 2014
Appl. No.: 13/597,612
Filed: Aug. 29, 2012

Related U.S. Application Data

(63) Continuation of application No. 12/862,489, filed on Aug. 24, 2010, now Pat. No. 8,279,586.

(60) Provisional application No. 61/236,800, filed on Aug. 25, 2009.

(51) Int. Cl.
*G06F 1/16* (2006.01)
*H05K 7/00* (2006.01)
*A61B 5/00* (2006.01)

(52) U.S. Cl.
CPC ............... *H05K 7/00* (2013.01); *A61B 5/00* (2013.01); *A61B 5/0002* (2013.01); *A61B 5/742* (2013.01); *A61B 2560/0456* (2013.01)

(58) Field of Classification Search
None
See application file for complete search history.

(56) References Cited

To view the complete listing of prior art documents cited during the proceeding for Reexamination Control Number 90/014,194, please refer to the USPTO's public Patent Application Information Retrieval (PAIR) system under the Display References tab.

*Primary Examiner* — Linh M Nguyen

(57) ABSTRACT

Patient monitoring systems can include a display unit and a patient parameter module. The patient parameter module can be connected to a docking region so as to communicate with the display unit in two or more orientations.

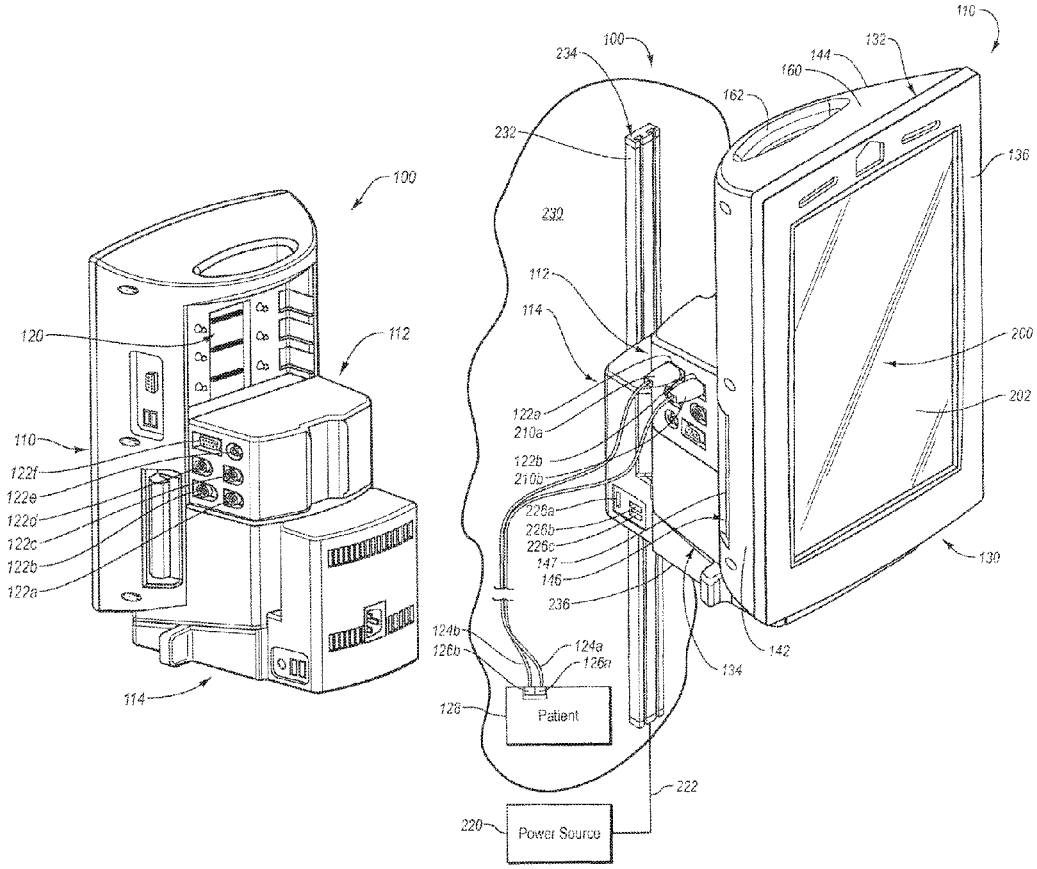

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9-11 and 29 are cancelled.

Claims 2, 3, 7, 12, 16, 18, 19-24 and 27 are determined to be patentable as amended.

Claims 4-6, 8, 13-15, 17, 25-26 and 28, dependent on an amended claim, are determined to be patentable.

New claims 30-78 are added and determined to be patentable.

2. The display system of claim [1] *58*, wherein the display unit comprises the docking region.

3. The display system of claim [1] *58*, wherein the docking region comprises a first connector and the module comprises a second connector, and wherein the first and second connectors are configured to couple with each other when the module is in each of the first and second orientations.

7. The display system of claim 3, wherein the first connector comprises a first non-electrical interface and the second connector comprises a second non-electrical interface, and wherein the first and second non-electrical interfaces are configured to couple with each other *to establish wired or tethered communication* when the module is in each of the first and second orientations.

12. The display system of claim [1] *58*, wherein the docking region comprises an electrical interface, and wherein the module comprises an electrical interface that is configured to couple with the electrical interface of the docking region when the module is in each of the first and second orientations.

16. The display system of claim [1] *58*, wherein the module comprises an actuator, and wherein actuation of the actuator permits disconnection of the module from the docking region.

18. The display system of claim [1] *58*, wherein the module is configured to be selectively connected with the docking region in one or more additional orientations in which the module is configured to provide information to the display unit via a linkage with the docking region.

19. The display system of claim [1] *58*, wherein the module is configured to be rotated by 180 degrees to transition from the first orientation to the second orientation.

20. The display system of claim [1] *58*, wherein a rack comprises the docking region, and wherein the rack is configured to electrically communicate with the display unit.

21. The display system of claim [1] *58*, wherein the module further comprises a display region configured to display information in each the first and second orientations without a preference for either orientation.

22. The display system of claim [1] *58*, wherein the module is configured to be wirelessly communicatively linked with the docking region in each of the first and second orientations.

23. The display system of claim [1] *58*, wherein the module comprises a sensor configured to detect one or both of an orientation of the module and a change in the orientation of the module.

24. A system configured to communicate information regarding a patient, the system comprising:
a docking region; and
a module configured *to* receive information via at least one communication passageway, the module configured to be selectively mechanically coupled with the docking region and to be selectively decoupled from the docking region, wherein the module is configured to be coupled with the docking region in either a first orientation or a second orientation,
wherein the docking region comprises a first connector and the module comprises a second connector, and wherein the first and second connectors are configured to couple with each other when the module is in each of the first and second orientations,
*wherein the module transmits identification information to the display unit to identify the module, and wherein the display system is a patient monitoring system.*

27. A patient parameter module configured to be selectively connected with a docking region in either a first orientation or a second orientation, wherein the docking region comprises a first side and a second side, the patient parameter module comprising:
a communication passageway configured to receive information regarding a patient from one or more sensors; and
a connector configured to electrically couple the module with the docking region when the module is in at least one of the first and second orientations,
[e;.4q]wherein when the module is connected to the docking region in the first orientation, the communication passageway is closer to the first side of the docking region than it is to the second side of the docking region, and wherein when the module is connected to the docking region in the second orientation, the communication passageway is closer to the second side of the docking region than it is to the first side of the docking region,
*wherein the module transmits identification information to the display unit to identify the module, and wherein the display system is a patient monitoring system.*

*30. The patient parameter module of claim 27, wherein transition of the patient parameter module from the first orientation to the second orientation causes an alteration of an electrical configuration of the connector.*

*31. The patient parameter module of claim 27, wherein the connector comprises a plurality of electrical contacts, and wherein movement of the module from the first orientation to the second orientation causes assignments of the electrical contacts to be rearranged.*

*32. The display system of claim 24, wherein an assignment of electrical contacts of one of the first and second connectors is configured to change when the module is transitioned between the first and second orientations, and wherein the display system is a patient monitoring system.*

*33. The display system of claim 58, wherein:
the docking region comprises a first connector;
the module comprises a second connector;
the docking region transfers power to the module via the first and second connector in each of the first and second orientations;* the module communicates information to the docking region via the first and second connector in each of the first and second orientations; and the display system is a patient monitoring system.

34. The display system of claim 33, wherein the first and second connectors each comprise an electrical interface configured to transfer the power and a non-electrical interface configured to communicate the information.

35. The display system of claim 34, wherein the non-electrical interface is configured to transmit optical signals.

36. A display system comprising:

a display unit;

a docking region configured to receive information used by the display unit, the docking region having a first side and a second side;

a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations, wherein the display unit is configured to display patient information obtained by a plurality of sensors, and the docking region comprises a plurality of connectors, the system comprising:

a plurality of modules, each module comprising a connector, wherein each module is configured to be selectively connected with the docking region and to be selectively disconnected from the docking region, wherein each module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, wherein each module is configured to be communicatively linked with the docking region in each of the first and second orientations, wherein each connector of a module is configured to couple with one of the plurality of connectors of the docking region in each of the first and second orientations, and wherein the display system is a patient monitoring system.

37. The display system of claim 36, wherein a first module is connected with the docking region in the first orientation simultaneously with a second module being connected with the docking region in the second orientation.

38. The display system of claim 36, wherein the display unit obtains information regarding whether a connector of the docking region is used or obstructed when a module is connected to the docking region.

39. The display system of claim 36, wherein the display unit obtains information regarding which module of the plurality of modules uses or obstructs a connector of the docking region.

40. A display system comprising:

a display unit;

a docking region configured to receive information used by the display unit, the docking region having a first side and a second side; and a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations, wherein the module comprises an actuator, wherein actuation of the actuator permits disconnection of the module from the docking region, and wherein the actuator is configured to disconnect the module from the docking region when actuated by a user in a direction away from the docking region when the module is connected with the docking region in either the first orientation or the second orientation, wherein the display system is a patient monitoring system.

41. The display system of claim 40, wherein:

the docking region comprises a mounting pin located between the first side and second side;

the module comprises:

an opening configured to receive the mounting pin when the module is connected with the docking region; and a latch configured to constrict a size of the opening when the mounting pin has been received so as to hold a portion of the mounting pin and maintain the module connected to the docking region.

42. The display system of claim 41, wherein translation of the actuator in the direction away from the docking region moves the latch to enlarge the opening and release the mounting pin when disconnecting the module from the docking region.

43. The display system of claim 41, wherein the latch is biased to constrict the size of the opening before the actuator has been actuated.

44. The display system of claim 41, wherein:

the actuator is located on a different side from a side on which the module is connected with the docking region in each of the first and second orientations.

45. A display system comprising:

a display unit;

a docking region configured to receive information used by the display unit, the docking region having a first side and a second side; and a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, wherein the module is configured to be communicatively linked with the docking region in each of the first and second orientations, wherein the module comprises at least one guide;

wherein the docking region comprises at least two channels configured to receive and retain the at least one guide when the module is connected with the docking region in either the first or second orientation, wherein the display system is a patient monitoring system.

46. The display system of claim 45, wherein the at least two channels comprise at least one channel on the first side of the docking region and at least one channel on the second side of the docking region.

47. The display system of claim 45, wherein the at least one guide comprises at least one protrusion.

48. A display system comprising:

a display unit;

a docking region configured to receive information used by the display unit, the docking region having a first side and a second side; and a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations, wherein the module comprises a structure configured for single-handed gripping of the module, and wherein the display system is a patient monitoring system.

49. The display system of claim 48, wherein the structure is one of a recess or a channel.

50. The display system of claim 48, wherein the structure is located on a side of the module opposite a side on which the module is connected with the docking region in each of the first and second orientations.

51. The display system of claim 48, further comprising an actuator configured to disconnect the module from the docking region, the actuator being located on a side face of the module, wherein the module is configured to be gripped by a single hand between the structure and the side face of the module that includes the actuator.

52. The display system of claim 58, wherein:

the docking region comprises a first electrical interface, the module comprises a second electrical interface, each of the first and second electrical interfaces comprises a plurality of electrical contacts, the module is configured to communicate information with the docking region through one or more of the electrical contacts of the first and second electrical interfaces when the first and second electrical interfaces are engaged in each of the first and second orientation.

53. A display system comprising:

a display unit;

a docking region configured to receive information used by the display unit, the docking region having a first side and a second side;

a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations; and, a base configured to host the docking region, wherein the base is further configured to communicate with the display unit, wherein the display system is a patient monitoring system.

54. The display system of claim 53, wherein the base is integrated with a rack comprising the docking region.

55. The display system of claim 53, wherein the base is configured to interface with a hospital network.

56. The display system of claim 53, wherein the base is fixed to a hospital bed.

57. The display system of claim 53, wherein the base is coupled to a mounting strip, the mounting strip being configured to be adjusted upwardly or downwardly along a channel.

58. A display system comprising:

a display unit;

a docking region configured to receive information used by the display unit, the docking region having a first side and a second side; and a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations, wherein the module transmits identification information to the display unit to identify the module, and wherein the display system is a patient monitoring system.

59. The display system of claim 58, wherein the identification information comprises at least one of manufacturer, model number, serial number, and date of manufacture.

60. The display system of claim 58, wherein the module is configured to communicate with the display unit wirelessly.

61. The display system of claim 58, wherein the module receives patient information transmitted from the display unit.

62. A display system comprising:

a display unit;

a docking region configured to receive information used by the display unit, the docking region having a first side and a second side; and a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations, wherein the module comprises a display region configured to define an orientation of the module.

63. A display system comprising:

a display unit;

a docking region configured to receive information used by the display unit, the docking region having a first side and a second side; and a module comprising a communication passageway, the module configured to be selectively connected with the docking region and to be selectively disconnected from the docking region, wherein the module is configured to be connected with the docking region in either a first orientation in which the communication passageway is closer to the first side of the docking region than it is to the second side of the docking region or a second orientation in which the communication passageway is closer to the second side of the docking region than it is to the first side of the docking region, and wherein the module is configured to be communicatively linked with the docking region in each of the first and second orientations, wherein one of the docking region and the module comprises both a first and a second electrical interface, wherein the first and second electrical interfaces are asymmetrical so as to indicate whether the module is in the first orientation or the second orientation.

64. The display system of claim 40, wherein the module further comprises a display region configured to display information in each the first and second orientations without a preference for either orientation.

65. The display system of claim 40, wherein the module is configured to be wirelessly communicatively linked with the docking region in each of the first and second orientations.

66. The display system of claim 40, wherein the module comprises a sensor configured to detect one or both of an orientation of the module and a change in the orientation of the module.

67. The display system of claim 69, wherein the module transmits identification information to the display unit to identify the module.

68. The display system of claim 45, wherein the module comprises an actuator, and wherein actuation of the actuator permits disconnection of the module from the docking region.

69. The display system of claim 45, wherein the module further comprises a display region configured to display information in each the first and second orientations without a preference for either orientation.

70. The display system of claim 45, wherein the module is configured to be wirelessly communicatively linked with the docking region in each of the first and second orientations.

71. The display system of claim 45, wherein the module comprises a sensor configured to detect one or both of an orientation of the module and a change in the orientation of the module.

72. The display system of claim 48, wherein the module transmits identification information to the display unit to identify the module.

73. The display system of claim 48, wherein the module comprises an actuator, and wherein actuation of the actuator permits disconnection of the module from the docking region.

74. The display system of claim 24, wherein the module comprises an actuator, wherein actuation of the actuator permits disconnection of the module from the docking region, and wherein the actuator is configured to disconnect the module from the docking region when actuated by a user in a direction away from the docking region when the module is connected with the docking region in either the first orientation or the second orientation.

75. The display system of claim 24, wherein the module comprises at least one guide, wherein the docking region comprises at least two channels configured to receive and retain the at least one guide when the module is connected with the docking region in either the first or second orientation.

76. The display system of claim 24, wherein the module comprises a structure configured for single-handed gripping of the module.

77. The display system of claim 24, wherein the first connector comprises a first non-electrical interface and the second connector comprises a second non-electrical interface, and wherein the first and second non-electrical interfaces are configured to couple with each other to establish wired or tethered communication when the module is in each of the first and second orientations.

78. The display system of claim 77, wherein the module is configured to provide information to the display unit via the first and second non-electrical interfaces when the module is in each of the first and second orientations.

* * * * *